US012800591B2

(12) United States Patent
Karl et al.

(10) Patent No.: US 12,800,591 B2
(45) Date of Patent: Nov. 17, 2026

(54) CIRCULATING BMP10 (BONE MORPHOGENIC PROTEIN 10) IN THE ASSESSMENT OF ATRIAL FIBRILLATION

(71) Applicants: Roche Diagnostics Operations, Inc., Indianapolis, IN (US); UNIVERSITEIT MAASTRICHT, LK Maastricht (NL); ACADEMISCH ZIEKENHUIS MAASTRICHT, HX Maastricht (NL)

(72) Inventors: Johann Karl, Penzberg (DE); Peter Kastner, Penzberg (DE); Ursula-Henrike Wienhues-Thelen, Penzberg (DE); Manuel Dietrich, Penzberg (DE); Andre Ziegler, Rotkreuz (CH); Ulrich Schotten, LK Maastricht (NL)

(73) Assignees: Roche Diagnostics Operations, Inc., Indianapolis, IN (US); Universiteit Maastricht, LK Maastricht (NL); Academisch Ziekenhuis Maastricht, HX Maastricht (NL)

( * ) Notice: Subject to any disclaimer, the term of this patent is extended or adjusted under 35 U.S.C. 154(b) by 1313 days.

(21) Appl. No.: 17/177,673

(22) Filed: Feb. 17, 2021

(65) Prior Publication Data

US 2021/0190801 A1 Jun. 24, 2021

Related U.S. Application Data

(63) Continuation of application No. PCT/EP2019/072042, filed on Aug. 16, 2019.

(30) Foreign Application Priority Data

Aug. 17, 2018 (EP) .................................... 18189551

(51) Int. Cl.
*G01N 33/68* (2006.01)
*G01N 33/577* (2006.01)

(52) U.S. Cl.
CPC ....... *G01N 33/6893* (2013.01); *G01N 33/577* (2013.01); *G01N 2496/00* (2013.01); *G01N 2800/325* (2013.01); *G01N 2800/326* (2013.01)

(58) Field of Classification Search
None
See application file for complete search history.

(56) References Cited

U.S. PATENT DOCUMENTS

| | | | | |
|---|---|---|---|---|
| 4,016,043 | A | 4/1977 | Schuurs et al. | |
| 4,018,653 | A | 4/1977 | Mennen | |
| 4,424,279 | A | 1/1984 | Bohn et al. | |
| 2006/0024783 | A1* | 2/2006 | Seehra | A61K 38/1875 514/17.4 |
| 2007/0092886 | A1* | 4/2007 | Tabibiazar | C12Q 1/6883 435/287.2 |
| 2009/0017019 | A1* | 1/2009 | Shields | A61P 13/12 435/375 |
| 2012/0183543 | A1* | 7/2012 | Buckler | A61P 21/00 435/6.12 |
| 2012/0213782 | A1 | 8/2012 | Seehra et al. | |
| 2013/0209490 | A1 | 8/2013 | Buckler et al. | |
| 2014/0286929 | A1 | 9/2014 | Kossen et al. | |
| 2015/0099399 | A1 | 4/2015 | Shimada | |
| 2018/0208648 | A1* | 7/2018 | Straub | A61P 35/02 |
| 2018/0280476 | A1* | 10/2018 | Buckler | A61K 38/1875 |

FOREIGN PATENT DOCUMENTS

| | | | |
|---|---|---|---|
| EP | 0648228 | B1 | 4/1998 |
| WO | 02/083913 | A1 | 10/2002 |
| WO | 02/089657 | A2 | 11/2002 |
| WO | 2010144358 | A1 | 12/2010 |
| WO | 2011008696 | A2 | 1/2011 |
| WO | 2012107419 | A1 | 8/2012 |
| WO | 2017216387 | A1 | 12/2017 |
| WO | 2018024905 | A1 | 2/2018 |
| WO | 2018229051 | A1 | 12/2018 |

OTHER PUBLICATIONS

Chen et al. "Analysis of Ventricular Hypertrabeculation and Noncompaction Using Genetically Engineered Mouse Modles" Pediatric Cardiology, vol. 30, No. 5, Apr. 25, 2009, pp. 626-663.*

Plotrowska, Izabela. "Functional implications of Bone Morphogenetic Protein 10 (BMP10) expression in pathological hearts". Inauguraldissertation zur Erlangung des Grades einesDoctors der Humanbiologie Des Fachbereichs Medizin Der Justus-Liebig-Universität Gießen. 2006.*

Nakano. "Interaction of BMP10 with Tcap may modulate the course of hypertensive cardiac hypertrophy" American Journal of Physiology; Heart and Circulatory Physiology, vo. 293, No. 6, Dec. 1, 2007, pp. H3396-H3403.*

Sun et al. "Bone Morphogenetic Protein-10 Induces Cardiomyocyte Proliferation and Improves Cardiac Function After Myocardial Infarction" Journal of Cellular Biochemistry (2014), 115(11), 1868-1876.*

(Continued)

*Primary Examiner* — Ann Montgomery
(74) *Attorney, Agent, or Firm* — Taft Stettinius & Hollister LLP

(57) ABSTRACT

The present invention relates to a method for assessing atrial fibrillation in a subject, said method comprising the steps of determining the amount of BMP 10 in a sample from the subject, and comparing the amount of BMP 10 to a reference amount, whereby atrial fibrillation is to be assessed. Moreover, the present invention relates to a method for diagnosing heart failure based on the determination of BMP 10 in a sample from a subject. Further, the present invention relates to a method for predicting the risk of a subject of hospitalization due to heart failure based on the determination of a BMP 10-type peptide in a sample from a subject.

16 Claims, 6 Drawing Sheets

Figure 1:
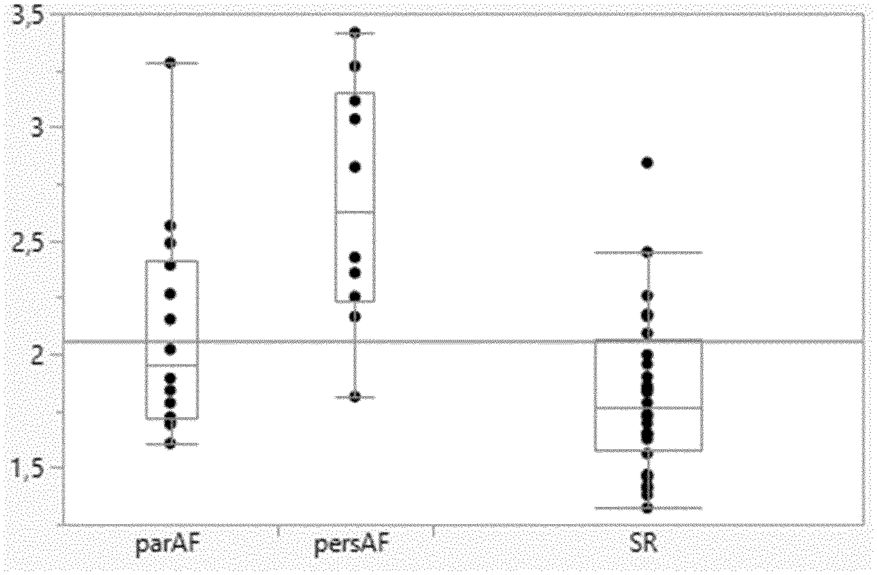

Specification includes a Sequence Listing.

(56) References Cited

OTHER PUBLICATIONS

Chinese Search Report; China National Intellectual Property Administration; Chinese Patent Application No. 201980054081.4; May 1, 2024; 2 pages.
International Search Report, European Patent Office, International Patent Application No. PCT/EP2019/072042, Dec. 3, 2019, 5 pages.
Written Opinion of the International Searching Authority, European Patent Office, International Patent Application No. PCT/EP2019/072042, Dec. 3, 2019, 7 pages.
International Preliminary Report on Patentability, European Patent Office, International Patent Application No. PCT/PCT/EP2019/072624, Nov. 2, 2020, 18 pages.
Dowdy et al., "Statistics for Research", 1983, John Wiley & Sons.
Fuster et al., 2011 ACCF/AHA/HRS Focused Updates Incorporated Into the ACC/AHA/ESC 2006 Guidelines for the Management of Patients With Atrial Fibrillation, Circulation, vol. 123, 2011, pp. e269-e367.
Hunt et al., ACC/AHA Guidelines for the Evaluation and Management of Chronic Heart Failure in the Adult: Executive Summary, J. Am. Coll. Cardiol., vol. 38, 2001, pp. 2101-2113.
Hunt et al., ACC/AHA 2005 Guideline Update for the Diagnosis and Management of Chronic Heart Failure in the Adult, Journal of the American College of Cardiology, vol. 46, No. 6, Sep. 20, 2005.
Anonymous: "Array-Based Gene Expression Analysis", Internet Citation, Apr. 10, 2013 (Apr. 10, 2013), pp. 1-5 Retrieved from the Internet: URL:https://web.archive.org/web/20130410192832/http:l/www.illumina.com/documents/products/datasheets/ datasheet_gene_exp_analysis.pdf.
International Preliminary Report on Patentability, European Patent Office, International Patent Application No. PCT/EP2019/072042, Nov. 30, 2020, 30 pages.
Japanese Notice of Allowance, Japan Patent Office, Japanese Patent Application No. 2021-532521, Feb. 1, 2023, 5 pages.
Chinchilla et al., "PITX2 Insufficiency Leads to Atrial Electrical and Structural Remodeling Linked to Arrythmogenesis", Circulation: Cardiovascular Genetics, vol. 4, No. 3, Apr. 21, 2011, pp. 269-279.
European Office Action, European Patent Office, European Patent Application No. 19752724.5, Mar. 11, 2024, 19 pages.
AAB02555.1 Fatty acid binding protein FABP [*Homo sapiens*], 1996, 1 p.
Bonow, Robert O., New Insights Into the Cardiac Natriuretic Peptides, Circulation, 1996, pp. 1946-1950, vol. 93.
Béchard, David et al., Endocan is a Novel Chondroitin Sulfate/Dermatan Sulfate Proteoglycan That Promotes Hepatocyte Growth Factor/Scatter Factor Mitogenic Activity, The Journal of Biological Chemistry, 2001, pp. 48341-48349, vol. 276, No. 51.
Chugh, Sumeet S. et al., Worldwide Epidemiology of Atrial Fibrillation A Global Burden of Disease 2010 Study, Circulation, 2014, pp. 837-847, vol. 129.
Conen, David et al., Design of the Swiss Atrial Fibrillation Cohort Study (Swiss-AF): structural brain damage and cognitive decline among patients with atrial fibrillation, Swiss Medical Weekly, 2017, 9 pp., vol. 147, vol. 14467.
David, Laurent et al., Identification of BMP9 and BMP10 as functional activators of the orphan activin receptor-like kinase 1 (ALK1) in endothelial cells, Blood, 2007, pp. 1953-1961, vol. 109.
Franco, Diego et al., Modulation of conductive elements by Pitx2 and their impact on atrial arrhythmogenesis, Cardiovascular Research, 2011, pp. 223-231, vol. 91.
Fuster, Valentin et al., ACC/AHA/ESC 2006 Guidelines for the Management of Patients With Atrial Fibrillation, Circulation, 2006, pp. e257-e354, vol. 114, No. 7.
Go, Alan S. et al., Prevalence of Diagnosed Atrial Fibrillation in Adults, JAMA, 2001, pp. 2370-2375, vol. 285.
Hanying Chen et al., Analysis of Ventricualr Hypertrabeculation and Noncompaction Using Genetically Engeneered Mouse Models, Pediatric Cardiology, 2009, pp. 626-634, vol. 30, No. 5.
Hart, Robert G. et al., Meta-analysis: Antithrombotic Therapy to Prevent Stroke in Patients Who Have Nonvalvular Atrial Fibrillation, Annals of Internal Medicine, 2007, pp. 857-867, vol. 146.
Hijazi, Ziad et al., The novel biomarker-based ABC (age, biomarkers, clinical history)—bleeding risk score for patients with atrial fibrillation: a derivation and validation study, The Lancet, 2016, 2302-2311, vol. 387.
Huang, Jianhe et al., Myocardin regulates BMP10 expression and is required for heart development, The Journal of Clinical Investigation, 2012, pp. 3678-3691, vol. 122, No. 10.
Jiang, He et al., The Prodomain-bound Form of Bone Morphogenetic Protein 10 is Biologically Active on Endothelial Cells, The Journal of Biological Chemistry, 2016, pp. 2954-2966, vol. 291, No. 6.
Kahr, Peter C. et al., Systemic Analysis of Gene Expression Differences between Left and Right Atria in Different Mouse Strains and in Human Atrial Tissue, PLoS One, 2010, 11 pp., vol. 6, No. 10, e26389.
Lassalle, Philippe et al., ESM-1 is a Novel Human Endothelial Cell-specific Molecule Expressed in Lung and Regulated by Cytokines, The Journal of Biological Chemistry, 1996, pp. 20458-20464, vol. 271, No. 34.
Latini, R. et al., Circulating cardiovascular biomarkers in recurrent atrial fibrillation: data from the GISSI-Atrial Fibrillation Trial, Journal of Internal Medicine, 2011, pp. 160-171, vol. 269.
Maisonpierre, Peter C. et al., Angiopoietin-2, a Natural Antagonist for Tie2 That Disrupts in vivo Angiogenesis, Science, 1997, pp. 55-60, vol. 277.
Nakano, Noritsugu et al., Interaction of BMP10 with Tcap may modulate the course of hypertensive cardiac hypertrophy, American Journal of Physiology: Heart and Circulatory Physiology, 2007, pp. H3396-H3403, vol. 293, No. 6.
Peeters, Roger A. et al., Cloning of the cDNA encoding human skeletal-muscle fatty-acid-binding protein, its peptide sequence and chromosomal localization, The Biochemical Journal, 1991, pp. 203-207, vol. 276, No. 1.
Piotrowska, Izabela, Functional implications of Bone Morphogenetic Protein 10 (BMP10) expression in pathological hearts, Dissertation to Obtain the Degree of Doctor of Human Biology from the Medical Department of the Justus-Liebig-Universitaet Giessen, retrieved from http://geb.uni-giessen.de/geb/volltexte/2007/4846/pdf/PiotrowskaIzabela2007-07-02, pp. 77-128 and 149-163.
Ricard, Nicolas et al., BMP9 and BMP10 are critical for postnatal retinal vascular remodeling, Blood, 2012, pp. 6162-6171, vol. 119, No. 25.
Richter, Mark M., Electrochemiluminescence (ECL), Chemical Reviews, 2004, pp. 3003-3036, vol. 104.
Storch, Judith and Thumser, Alfred E. A., The fatty acid transport function of fatty acid-binding proteins, Biochimica et Biophysica Acta, 2000, pp. 28-44, vol. 1486.
Sun, Lijun et al., Bone Morphogenetic Protein-10 Induces Cardiomyocyte Proliferation and Improves Cardiac Function After Myocardial Infarction, Journal of Cellular Biochemistry, 2014, pp. 1868-1876, vol. 115.
Susan-Resiga, Delia et al., Furin is the Major Processing Enzyme of the Cardiac-specific Growth Factor Bone Morphogenetic Protein 10, The Journal of Biological Chemistry, 2011, pp. 22785-22794, vol. 286, No. 26.
Syeda, Fahima et al., PITX2-dependent gene regulation in atrial fibrillation and rhythm control, The Journal of Physiology, 2017, pp. 4019-4026, vol. 595, No. 12.
Tessari, Alessandra et al., Myocardial Pitx2 Differentially Regulates the Left Atrial Identity and Ventricular Asymmetric Remodeling Programs, Circulation Research, 2008, pp. 813-822, vol. 102, No. 7.
U57623.1 Human fatty acid binding protein FABP gene, complete cds, 1996, 3 pp.
Uhlén, Mathias et al., Tissue-based map of the human proteome, Science, 2015, pp. 126049-1-126049-9, vol. 347, No. 6220.
UniProtKB O15123 (ANGP2_Human) Angiopoietin-2, 1998, 3 pp.
UniProtKB O15123-2 (ANGP2_Human) Angiopoietin-2, 1998, 3 pp.
UniProtKB O15123-3 (ANGP2_Human) Angiopoietin-2, 1998, 3 pp.
UniProtKB O95393-1 (BMP 10_Human) Bone morphogenetic protein 10, 1999, 2 pp.

(56) References Cited

OTHER PUBLICATIONS

UniProtKB Q9NQ30 (ESM1_Human) Endothelial cell-specific molecule 1, 2001, 2 pp.
UniProtKB Q9NQ30 (ESM1_Human) Endothelial cell-specific molecule 1, None, 2001, 3 pp.
Yadin, David et al., Structural insights into BMP receptors: Specificity, activation and inhibition, Cytokine & Growth Factor Reviews, 2016, pp. 13-34, vol. 27.
Zweig, Mark H. and Campbell, Gregory, Receiver-Operating Characteristic (ROC) Plots: A Fundamental Evaluation Tool in Clinical Medicine, Clinical Chemistry, 1993, pp. 561-577, vol. 39, No. 4.
Chen et al., Analysis of Ventricular Hypertrabeculation and Noncompaction Using Genetically Engineered Mouse Models; Peditr Cardiol, 2009, vol. 30, pp. 626-634.
ACC/AHA/ESC Practice Guidelines; 2006, 99-pages.
Feng, Ou; Identification and Prediction of Biological Features Associated with Atrial Fibrillation; A Master Thesis Submitted to University of Electronic Science and Technology of China; School of Life Science and Technology; 1994-2022 China Academic Journal Electronic Publishing House. pp. 1-55 (English Abstract only).

* cited by examiner

Number at risk

| | 0 | 500 | 1000 | 1500 |
|---|---|---|---|---|
| BMP−10 [1.179,2.054] | 154 | 118 | 57 | 0 |
| BMP−10 (2.054,2.3925] | 149 | 110 | 62 | 2 |
| BMP−10 (2.3925,2.9005] | 151 | 115 | 54 | 0 |
| BMP−10 (2.9005,6.987] | 152 | 93 | 46 | 3 |

CIRCULATING BMP10 (BONE MORPHOGENIC PROTEIN 10) IN THE ASSESSMENT OF ATRIAL FIBRILLATION

This application is a continuation application based on International Patent Application Serial No. PCT/EP2019/072042 (published as WO 2020/035605), filed Aug. 16, 2019, which claims priority from EP 18189551.7, filed Aug. 17, 2018, both of which are hereby incorporated by reference in their entirety.

The present invention relates to a method for assessing atrial fibrillation in a subject, said method comprising the steps of determining the amount of a BMP10-type peptide in a sample from the subject, and comparing the amount of the BMP10-type peptide to a reference amount, whereby atrial fibrillation is to be assessed. Moreover, the present invention relates to a method for diagnosing heart failure based on the determination of a BMP10-type peptide in a sample from a subject. Further, the present invention relates to a method for predicting the risk of a subject of hospitalization due to heart failure based on the determination of a BMP10-type peptide in a sample from a subject.

BACKGROUND SECTION

Atrial fibrillation (AF) is the most common type of heart arrhythmia and one of the most widespread conditions among the elderly population. Atrial fibrillation is characterized by irregular heart beating and often starts with brief periods of abnormal beating that can increase over time and may become a permanent condition. An estimated 2.7-6.1 million people in the United States have Atrial Fibrillation and approximately 33 million people globally (Chugh S. S. et al., Circulation 2014; 129:837-47).

The diagnosis of heart arrhythmia such as atrial fibrillation typically involves determination of the cause of the arrhythmia, and classification of the arrhythmia. Guidelines for the classification of atrial fibrillation according to the American College of Cardiology (ACC), the American Heart Association (AHA), and the European Society of Cardiology (ESC) are mainly based on simplicity and clinical relevance. The first category is called "first detected AF". People in this category are initially diagnosed with AF and may or may not have had previous undetected episodes. If a first detected episode stops on its own in less than one week, but is followed by another episode later on, the category changes to "paroxysmal AF". Although patients in this category have episodes lasting up to 7 days, in most cases of paroxysmal AF the episodes will stop in less than 24 hours. If the episode lasts for more than one week, it is classified as "persistent AF". If such an episode cannot be stopped, i.e. by electrical or pharmacologic cardioversion, and continues for more than one year, the classification is changed to "permanent AF". An early diagnosis of atrial fibrillation is highly desired because atrial fibrillation is an important risk factor for stroke and systemic embolism (Hart et al., Ann Intern Med 2007; 146(12): 857-67; Go A S et al. JAMA 2001; 285(18): 2370-5). Stroke ranks after ischemic heart disease second as a cause of lost disability—adjusted—life years in high income countries and as a cause of death worldwide. In order to reduce the risk of stroke, anticoagulation therapy appears the most appropriate therapy.

Biomarkers which allow for the assessment of atrial fibrillation are highly desired.

Latini R. et al. (J Intern Med. 2011 February; 269(2): 160-71) measured various circulating biomarkers (hsTnT, NT-proBNP, MR-proANP, MR-proADM, copeptin, and CT-proendothelin-1) in patients with atrial fibrillation.

Bone Morphogenic Protein 10 (abbreviated BMP10) is a ligand of the TGF-beta (transforming growth factor-beta) superfamily of proteins. Ligands of this family bind various TGF-beta receptors leading to recruitment and activation of certain transcription factors that regulate gene expression. BMP10 binds to the activin receptor-like kinase 1 (ALKi) and has been shown to be a functional activator of this kinase in in endothelial cells (David et al., Blood. 2007, 109(5):1953-61).

BMP10 is synthesized as an inactive precursor protein (pro-BMP10, ~60 kDa) that is activated by proteolytic cleavage resulting in the non-glycosylated C-terminal peptide of 108 aa (~14 kDa; BMP10) and an N-terminal prosegment of ~50 kDa (Susan-Resiga et al., J Biol Chem. 2011 Jul. 1; 286(26):22785-94). Both remain in structural proximity forming homo- or hetero-dimers of BMP10 or in combination with other BMP-family proteins (Yadin et al., CYTOGFR 2016, 27 (2016) 13-34). The dimerization occurs by formation of Cys-Cys bridge or strong adhesion in the C-terminal peptides of both binding partners. Thus, an architecture consisting of two subunits is formed.

It has been shown that BMP10 plays a role in cardiovascular development including cardiomyocyte proliferation and regulation of heart size, closure of the ductus arteriosus, angiogenesis and ventricular trabeculation.

Being involved in the regulation of tissue repair, soluble BMP10 has been found as a diagnostic and treatment target involved in tissue fibrosis also in cardiovascular diseases (see e.g. US2013209490) Involvement of BMP10 has been described in vascular fibrosis and cardiac fibrosis.

US 2012/0213782 discloses BMP10 propeptides can be used for treating heart disorders.

A general role of BMP10 is in developmental regulation of vascular remodeling (Ricard et al., Blood. 2012 Jun. 21; 119(25): 6162-6171). Moreover, BMP10 is a heart developmental factor (Huang et al., J Clin Invest. 2012; 122(10): 3678-3691) and induces cardiomyocyte proliferation upon myocardial infarction (Sun et al., J Cell Biochem. 2014; 115(11)_1868-1876). It is described to also originate from endothelial cells (Jiang et al., JBC 2016, 291(6): 2954-2966).

Transcriptomic analyses reveal that BMP10 mRNA in healthy conditions is strongly expressed in heart right atrium and right atrial appendage. It is expressed predominantly in the right compare to the left atrial appendage (Kahr et al., Plos ONE, 2010, 6(10): e26389).

So far, circulating BMP10-type peptides have not been associated with atrial fibrillation.

There is a need for reliable methods for the assessment of atrial fibrillation including the diagnosis of atrial fibrillation, the risk stratification of patients with atrial fibrillation (such as occurrence of stroke), the assessment of the severity of atrial fibrillation, and the assessment of a therapy in patients with atrial fibrillation.

The technical problem underlying the present invention can be seen as the provision of methods for complying with the aforementioned needs. The technical problem is solved by the embodiments characterized in the claims and herein below.

Advantageously, it was found in the context of the studies of the present invention that the determination of the amount of a BMP10-type peptide in a sample from a subject allows for an improved assessment of atrial fibrillation. Thanks to present invention, it can be e.g. diagnosed whether a subject suffers from atrial fibrillation, or is at risk of suffering from stroke associated with atrial fibrillation.

SUMMARY OF THE PRESENT INVENTION

The present invention relates to a method for assessing atrial fibrillation in a subject, comprising the steps of a) determining, in at least one sample from the subject, the amount of a BMP10-type peptide (Bone Morphogenic Protein 10-type peptide) and, optionally, the amount of at least one further biomarker selected from the group consisting of a natriuretic peptide, ESM-1 (Endocan), Ang2 (Angiopoietin 2) and FABP3 (Fatty Acid Binding Protein 3), and b) comparing the amount of the BMP10-type peptide to a reference amount for the BMP10-type peptide and, optionally, comparing the amount of the at least one further biomarker to a reference amount for said at least one further biomarker, whereby atrial fibrillation is to be assessed.

The present invention further relates to a method of aiding in the assessment of atrial fibrillation, said method comprising the steps of:

a) providing at least one sample from a subject, b) determining, in the at least one sample provided in step a), the amount of a BMP10-type peptide (Bone Morphogenic Protein 10-type peptide) and, optionally, the amount of at least one further biomarker selected from the group consisting of a natriuretic peptide, ESM-1 (Endocan), Ang2 and FABP3 (Fatty Acid Binding Protein 3), and c) providing information on the determined amount of the BMP10-type peptide and optionally on the determined amount of the at least one further biomarker to a physician, thereby aiding in the assessment of atrial fibrillation.

Further, the present invention contemplates a method for aiding in the assessment of atrial fibrillation, comprising:

a) providing an assay for a BMP10-type peptide and, optionally, at least one further assay for a further biomarker selected from the group consisting of a natriuretic peptide, ESM-1 (Endocan), Ang2 and FABP3 (Fatty Acid Binding Protein 3), and b) providing instructions for using of the assay results obtained or obtainable by said assay(s) in the assessment of atrial fibrillation.

Also encompassed by the present invention is computer-implemented method for assessing atrial fibrillation, comprising a) receiving, at a processing unit, a value for the amount of a BMP10-type peptide, and, optionally at least one further value for the amount of at least one further biomarker selected from the group consisting of a natriuretic peptide, ESM-1 (Endocan), Ang2 and FABP3 (Fatty Acid Binding Protein 3), wherein said amount of BMP10 and, optionally, the amount of the at least one further biomarker have been determined in a sample from a subject, b) comparing, by said processing unit, the value or values received in step (a) to a reference or to references, and c) assessing atrial fibrillation based in the comparison step b).

The present invention further relates to a method for diagnosing heart failure, said method comprising the steps of (a) determining, in at least one sample from the subject, the amount of a BMP10-type peptide (Bone Morphogenic Protein 10-type peptide) and, optionally, the amount of at least one further biomarker selected from the group consisting of a natriuretic peptide, ESM-1 (Endocan), Ang2, and FABP3 (Fatty Acid Binding Protein 3), and (b) comparing the amount of the BMP10-type peptide to a reference amount for the BMP10-type peptide and, optionally, comparing the amount of the at least one further biomarker to a reference amount for said at least one further biomarker, whereby heart failure is to be diagnosed.

The present invention further relates to a method for predicting the risk of a subject of hospitalization due to heart failure, said method comprising the steps of (a) determining, in at least one sample from the subject, the amount of a BMP10-type peptide (Bone Morphogenic Protein 10-type peptide) and, optionally, the amount of at least one further biomarker selected from the group consisting of a natriuretic peptide, ESM-1 (Endocan), Ang2, and FABP3 (Fatty Acid Binding Protein 3), (b) comparing the amount of the BMP10-type peptide to a reference amount and, optionally, comparing the amount of the at least one further biomarker to a reference amount for said at least one further biomarker, and (c) predicting the risk of a subject of hospitalization due to heart failure.

The present invention further relates to a kit comprising an agent which specifically binds to a BMP10-type peptide and at least one further agent selected from the group consisting of an agent which specifically binds to a natriuretic peptide, an agent which specifically binds to ESM-1, an agent which specifically binds Ang2 and an agent which specifically binds to FABP3.

Moreover, the present invention relates to the in vitro use of i) a BMP10-type peptide and optionally of at least one further biomarker selected from the group consisting of a natriuretic peptide, ESM-1 (Endocan), Ang2 and FABP3 (Fatty Acid Binding Protein 3), and/or ii) at least one agent that specifically binds to a BMP10-type peptide, and, optionally, at least one further agent selected from the group consisting of an agent which specifically binds to a natriuretic peptide, an agent which specifically binds to ESM-1, an agent which specifically binds to Ang2 and an agent which specifically binds to FABP3, for assessing atrial fibrillation, for predicting the risk of stroke, or for diagnosing heart failure, or for predicting the risk of a subject of hospitalization due to heart failure.

DETAILED SUMMARY OF THE PRESENT INVENTION/DEFINITIONS

The present invention relates to a method for assessing atrial fibrillation in a subject, comprising the steps of a) determining, in at least one sample from the subject, the amount of a BMP10-type peptide (Bone Morphogenic Protein 10-type peptide), and b) comparing the amount of the BMP10-type peptide to a reference amount for the BMP10-type peptide, whereby atrial fibrillation is to be assessed.

The BMP10-type peptide is preferably selected from the group consisting of BMP10, N-terminal prosegment of BMP10 (N-terminal proBMP10), proBMP10, and preproBMP10. More preferably, the BMP10-type peptide is BMP10 and/or N-terminal proBMP10.

In an embodiment of method of the present invention, the method further comprises the determination of the amount of at least one further biomarker selected from the group consisting of a natriuretic peptide, ESM-1 (Endocan), Ang2 (Angiopoietin 2) and FABP-3 (Fatty acid binding protein 3) in a sample from the subject in step a) and the comparison of the amount of the at least one further biomarker to a reference amount in step b).

Accordingly, the present invention relates to a method for assessing atrial fibrillation in a subject, comprising the steps of a) determining, in at least one sample from the subject, the amount of a BMP10-type peptide (Bone Morphogenic Protein 10-type peptide) and, optionally, the amount of at least one further biomarker selected from the group consisting of a natriuretic peptide, ESM-1 (Endocan), Ang2 (Angiopoietin 2) and FABP-3 (Fatty acid binding protein 3), and
b) comparing the amount of the BMP10-type peptide to a reference amount for the BMP10-type peptide and, optionally, comparing the amount of the at least one further biomarker to a reference amount for said at least one further biomarker, whereby atrial fibrillation is to be assessed.

The assessment of atrial fibrillation (AF) shall be based on the results of the comparison step b).

Accordingly, the present invention preferably comprises the steps of a) determining, in at least one sample from the subject, the amount of a BMP10-type peptide and, optionally, the amount of at least one further biomarker selected from the group consisting of a natriuretic peptide, ESM-1 (Endocan), Ang2 (Angiopoietin 2) and FABP-3 (Fatty acid binding protein 3),
b) comparing the amount of the BMP10-type peptide to a reference amount for the BMP10-type peptide and, optionally, comparing the amount of the at least one further biomarker to a reference amount for said at least one further biomarker, and
c) assessing atrial fibrillation based on the results of the comparison step b).

The method as referred to in accordance with the present invention includes a method which essentially consists of the aforementioned steps or a method which includes further steps. Moreover, the method of the present invention, preferably, is an ex vivo and more preferably an in vitro method. Moreover, it may comprise steps in addition to those explicitly mentioned above. For example, further steps may relate to the determination of further markers and/or to sample pre-treatments or evaluation of the results obtained by the method. The method may be carried out manually or assisted by automation. Preferably, step (a), (b) and/or (c) may in total or in part be assisted by automation, e.g., by a suitable robotic and sensory equipment for the determination in step (a) or a computer-implemented calculation in step (b).

In accordance with the present invention, atrial fibrillation shall be assessed. The term "assessing atrial fibrillation" as used herein preferably refers to the diagnosis of atrial fibrillation, the differentiation between paroxysmal and persistent atrial fibrillation, the prediction of a risk of an adverse event associated with atrial fibrillation (such as stroke), to the identification of a subject who shall be subjected to electrocardiography (ECG), or to the assessment of a therapy for atrial fibrillation.

As will be understood by those skilled in the art, the assessment of the present invention is usually not intended to be correct for 100% of the subjects to be tested. The term, preferably, requires that a correct assessment (such as the diagnosis, differentiation, prediction, identification or assessment of a therapy as referred to herein) can be made for a statistically significant portion of subjects. Whether a portion is statistically significant can be determined without further ado by the person skilled in the art using various well known statistic evaluation tools, e.g., determination of confidence intervals, p-value determination, Student's t-test, Mann-Whitney test etc. Details are found in Dowdy and Wearden, Statistics for Research, John Wiley & Sons, New York 1983. Preferred confidence intervals are at least 90%, at least 95%, at least 97%, at least 98%, or at least 99%. The p-values are, preferably, 0.4, 0.1, 0.05, 0.01, 0.005, or 0.0001.

In accordance with the present invention, the expression "assessment of atrial fibrillation" is understood as an aid in the assessment of atrial fibrillation, and thus as an aid in diagnosing atrial fibrillation, an aid in differentiating between paroxysmal and persistent atrial fibrillation, an aid in the prediction of a risk of an adverse event associated with atrial fibrillation, an aid in the identification of a subject who shall be subjected to electrocardiography (ECG), or as an aid in the assessment of a therapy for atrial fibrillation. The final diagnosis, in principle, will be carried out by physician.

In a preferred embodiment of the present invention, the assessment of atrial fibrillation is the diagnosis of atrial fibrillation. Accordingly, it is diagnosed, whether a subject suffers from atrial fibrillation, or not.

Accordingly, the present invention envisages a method for diagnosing atrial fibrillation in a subject, comprising the steps of a) determining the amount of a BMP10-type peptide in a sample from the subject, and
b) comparing the amount of the BMP10-type peptide to a reference amount, whereby atrial fibrillation is to be diagnosed.

In an embodiment, the aforementioned method comprises the steps of:

(a) determining, in at least one sample from the subject, the amount of a BMP10-type peptide (Bone Morphogenic Protein 10) and, optionally, the amount of at least one further biomarker selected from the group consisting of a natriuretic peptide, ESM-1 (Endocan), Ang2 (Angiopoietin 2) and FABP-3 (Fatty acid binding protein 3), and
(b) comparing the amount of the BMP10-type peptide to a reference amount for the BMP10-type peptide and, optionally, comparing the amount of the at least one further biomarker to a reference amount for said at least one further biomarker, whereby atrial fibrillation is to be diagnosed.

Preferably, the subject to be tested in connection with method for diagnosing of atrial fibrillation is a subject who is suspected to suffer from atrial fibrillation. However, it is also contemplated that the subject already has been diagnosed previously to suffer from AF and that the previous diagnosis is confirmed by carrying out the method of the present invention.

In another preferred embodiment of the present invention, the assessment of atrial fibrillation is the differentiation between paroxysmal and persistent atrial fibrillation. Accordingly, it is determined whether a subject suffers from the paroxysmal or persistent atrial fibrillation.

Accordingly, the present invention envisages a method for differentiating between paroxysmal and persistent atrial fibrillation in a subject, comprising the steps of a) determining the amount of a BMP10-type peptide in a sample from the subject, and
b) comparing the amount of the BMP10-type peptide to a reference amount, whereby it is differentiated between paroxysmal and persistent atrial fibrillation.

In an embodiment, the aforementioned method comprises the steps of:

a) determining, in at least one sample from the subject, the amount of a BMP10-type peptide (Bone Morphogenic Protein 10) and, optionally, the amount of at least one further biomarker selected from the group consisting of a natriuretic peptide, ESM-1 (Endocan), Ang2 (Angiopoietin 2) and FABP-3 (Fatty acid binding protein 3), and
b) comparing the amount of the BMP10-type peptide to a reference amount for the BMP10-type peptide and, optionally, comparing the amount of the at least one further biomarker to a reference amount for said at least one further biomarker, whereby it is differentiated between paroxysmal and persistent atrial fibrillation.

In another preferred embodiment of the present invention, the assessment of atrial fibrillation is the prediction of the risk of an adverse event associated with atrial fibrillation (such as stroke). Accordingly, it is predicted whether a subject is at risk and/or not as risk of said adverse event.

Thus, the present invention envisages a method for predicting the risk of an adverse event associated with atrial fibrillation in a subject, comprising the steps of a) determining the amount of a BMP10-type peptide in a sample from the subject, and
b) comparing the amount of the BMP10-type peptide to a reference amount, whereby the risk of the adverse event associated with atrial fibrillation is to be predicted.

In an embodiment, the aforementioned method comprises the steps of:

a) determining, in at least one sample from the subject, the amount of a BMP10-type peptide (Bone Morphogenic Protein 10) and, optionally, the amount of at least one further biomarker selected from the group consisting of a natriuretic peptide, ESM-1 (Endocan), Ang2 (Angiopoietin 2) and FABP-3 (Fatty acid binding protein 3), and
b) comparing the amount of the BMP10-type peptide to a reference amount for the BMP10-type peptide and, optionally, comparing the amount of the at least one further biomarker to a reference amount for said at least one further biomarker, whereby the risk of the adverse event associated with atrial fibrillation is to be predicted.

It is envisaged that various adverse events can be predicted. A preferred adverse event to be predicted is stroke.

Accordingly, the present invention, in particular, contemplates a method for predicting the risk of stroke in a subject, comprising the steps of a) determining the amount of a BMP10-type peptide in a sample from the subject, and
b) comparing the amount of the BMP10-type peptide to a reference amount, whereby the risk of stroke is to be predicted.

The aforementioned method may further comprise step c) of predicting stroke based on the comparison results of step b). Thus, steps a), b), c) are preferably as follows:

a) determining the amount of a BMP10-type peptide in a sample from the subject, and
b) comparing the amount of the BMP10-type peptide to a reference amount, and
c) predicting stroke based on the comparison results of step b)

In another preferred embodiment of the present invention, the assessment of atrial fibrillation is the assessment of a therapy for atrial fibrillation.

Accordingly, the present invention envisages a method for the assessment of a therapy for atrial fibrillation in a subject, comprising the steps of a) determining the amount of a BMP10-type peptide in a sample from the subject, and
b) comparing the amount of the BMP10-type peptide to a reference amount, whereby the therapy for atrial fibrillation is to be assessed.

In an embodiment, the aforementioned method comprises the steps of:

a) determining, in at least one sample from the subject, the amount of a BMP10-type peptide (Bone Morphogenic Protein 10) and, optionally, the amount of at least one further biomarker selected from the group consisting of a natriuretic peptide, ESM-1 (Endocan), Ang2 (Angiopoietin 2) and FABP-3 (Fatty acid binding protein 3), and
b) comparing the amount of the BMP10-type peptide to a reference amount for the BMP10-type peptide and, optionally, comparing the amount of the at least one further biomarker to a reference amount for said at least one further biomarker, whereby the therapy for atrial fibrillation is to be assessed.

Preferably, the subject in connection with the aforementioned differentiation, the aforementioned prediction, and the assessment of a therapy for atrial fibrillation is a subject who suffers from atrial fibrillation, in particular who is known to suffer from atrial fibrillation (and thus to have a known history of atrial fibrillation). However, with respect to the aforementioned prediction method, it is also envisaged that the subject has no known history of atrial fibrillation.

In another preferred embodiment of the present invention, the assessment of atrial fibrillation is the identification of a subject who shall be subjected to electrocardiography (ECG). Accordingly, a subject is identified who is who shall be subjected to electrocardiography, or not.

The method may comprise the steps of a) determining, in at least one sample from the subject, the amount of a BMP10-type peptide (Bone Morphogenic Protein 10) and, optionally, the amount of at least one further biomarker selected from the group consisting of a natriuretic peptide, ESM-1 (Endocan), Ang2 (Angiopoietin 2) and FABP-3 (Fatty acid binding protein 3), and
b) comparing the amount of the BMP10-type peptide to a reference amount for the BMP10-type peptide and, optionally, comparing the amount of the at least one further biomarker to a reference amount for said at least one further biomarker, whereby a subject is identified who shall be subjected to electrocardiography.

Preferably, the subject in connection with the aforementioned method of identifying a subject who shall be subjected to electrocardiography is a subject who has no known history of atrial fibrillation. The expression "no known history of atrial fibrillation" is defined elsewhere herein.

In another preferred embodiment of the present invention, the assessment of atrial fibrillation is the assessment of efficacy of an anticoagulation therapy of a subject. Accordingly, the efficacy of said therapy is assessed.

In another preferred embodiment of the present invention, the assessment of atrial fibrillation is the prediction of the risk of stroke in a subject. Accordingly, it is predicted whether a subject as referred to herein is at risk of stroke, or not.

In another preferred embodiment of the present invention, the assessment of atrial fibrillation is the identification a subject being eligible to the administration of at least one anticoagulation medicament or being eligible for increasing the dosage of at least one anticoagulation medicament. Accordingly, it is assessed whether a subject is eligible to said administration and/or said increase of the dosage.

In another preferred embodiment of the present invention, the assessment of atrial fibrillation is the monitoring of anticoagulation therapy. Accordingly, it is assessed whether a subject responds to said therapy, or not.

The term "atrial fibrillation" ("abbreviated" AF or AFib) is well known in the art. As used herein, the term preferably refers to a supraventricular tachyarrhythmia characterized by uncoordinated atrial activation with consequent deterioration of atrial mechanical function. In particular, the term refers to an abnormal heart rhythm characterized by rapid and irregular beating. It involves the two upper chambers of the heart. In a normal heart rhythm, the impulse generated by the sino-atrial node spreads through the heart and causes contraction of the heart muscle and pumping of blood. In atrial fibrillation, the regular electrical impulses of the sino-atrial node are replaced by disorganized, rapid electrical impulses which result in irregular heart beats. Symptoms of atrial fibrillation are heart palpitations, fainting, shortness of breath, or chest pain. However, most episodes have no symptoms. On the electrocardiogram, Atrial Fibrillation is characterized by the replacement of consistent P waves by rapid oscillations or fibrillatory waves that vary in amplitude, shape, and timing, associated with an irregular, frequently rapid ventricular response when atrioventricular conduction is intact.

Figure 3:
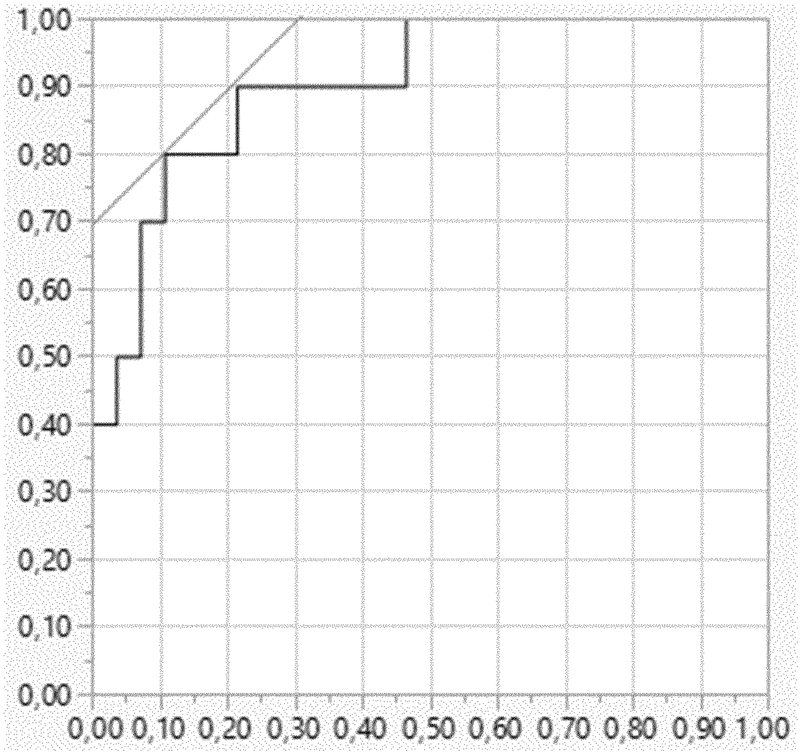

The American College of Cardiology (ACC), American Heart Association (AHA), and the European Society of Cardiology (ESC) propose the following classification system (see Fuster V. et al., Circulation 2006; 114 (7): e257-354 which herewith is incorporated by reference in its entirety, see e.g. FIG. 3 in the document): First detected AF, paroxysmal AF, persistent AF, and permanent AF.

All people with AF are initially in the category called first detected AF. However, the subject may or may not have had previous undetected episodes. A subject suffers from permanent AF, if the AF has persisted for more than one year, and in particular, conversion back to sinus rhythm does not occur (or only with medical intervention). A subject suffers from persistent AF, if the AF lasts more than 7 days. The subject may require either pharmacologic or electrical intervention to terminate Atrial Fibrillation. Preferably, persistent AF occurs in episodes, but the arrhythmia does not convert back to sinus rhythm spontaneously (i.e. without medical intervention). Paroxysmal Atrial Fibrillation, preferably, refers to an intermittent episode of Atrial Fibrillation which lasts up to 7 days. In most cases of paroxysmal AF, the episodes last less than 24 hours. The episode of Atrial Fibrillation terminates spontaneously, i.e. without medical intervention. Thus, whereas the episode(s) of paroxysmal atrial fibrillation preferably terminate spontaneously, persistent atrial fibrillation preferably does not end spontaneously. Preferably, persistent atrial fibrillation requires electrical or pharmacological cardioversion for termination, or other procedures, such as ablation procedures (Fuster V. et al., Circulation 2006; 114 (7): e257-354). Both persistent and paroxysmal AF may be recurrent, whereby distinction of paroxysmal and persistent AF is provided by ECG recordings: When a patient has had 2 or more episodes, AF is considered recurrent. If the arrhythmia terminates spontaneously, AF, in particular recurrent AF, is designated paroxysmal. AF is designated persistent if it lasts more than 7 days.

In a preferred embodiment of the present invention, the term "paroxysmal atrial fibrillation" is defined as episodes of AF that terminate spontaneously, wherein said episodes last less than 24 hours. In an alternative embodiment, the episodes which terminate spontaneously last up to seven days.

The "subject" as referred to herein is, preferably, a mammal. Mammals include, but are not limited to, domesticated animals (e.g., cows, sheep, cats, dogs, and horses), primates (e.g., humans and non-human primates such as monkeys), rabbits, and rodents (e.g., mice and rats). Preferably, the subject is a human subject.

Preferably, the subject to be tested is of any age, more preferably, the subject to be tested is 50 years of age or older, more preferably 60 years of age or older, and most preferably 65 years of age or older. Further, it is envisaged that the subject to be tested is 70 years of age or older.

Moreover, it is envisaged that the subject to be tested is 75 years of age or older. Also, the subject may be between 50 and 90 years.

In a preferred embodiment of the method of assessing atrial fibrillation, the subject to be tested shall suffer from atrial fibrillation. Accordingly, the subject shall have a known history of atrial fibrillation. Thus, the subject shall have experienced episodes of Atrial Fibrillation prior to obtaining the test sample, and at least one of the previous episodes of atrial fibrillation shall have been diagnosed, e.g. by ECG. For example, it is envisaged that the subject suffers from atrial fibrillation, if the assessment of atrial fibrillation is the differentiation between paroxysmal and persistent atrial fibrillation, or if the assessment of atrial fibrillation is the prediction of a risk of an adverse event associated with atrial fibrillation, or if the assessment of atrial fibrillation is the assessment of a therapy for atrial fibrillation.

In another preferred embodiment of the method of assessing atrial fibrillation, the subject to be tested is suspected to suffer from atrial fibrillation, e.g. if the assessment of atrial fibrillation is the diagnosis of atrial fibrillation or the identification of a subject who shall be subjected to electrocardiography (ECG).

Preferably, a subject who is suspected to suffer from atrial fibrillation is a subject who has shown at least one symptom of atrial fibrillation prior to carrying out the method for assessing atrial fibrillation. Said symptoms are usually transient and may arise in a few seconds and may disappear just as quickly. Symptoms of atrial fibrillation include dizziness, fainting, shortness of breath and, in particular, heart palpitations. Preferably, the subject has shown at least one symptom of atrial fibrillation within six months prior to obtaining the sample.

Alternatively or additionally, a subject who is suspected to suffer from atrial fibrillation shall be a subject who is 70 years of age or older.

Preferably, the subject who is suspected to suffer from atrial fibrillation shall have no known history of atrial fibrillation.

In accordance with the present invention, a subject having no known history of atrial fibrillation is, preferably, a subject who has not been diagnosed to suffer from atrial fibrillation previously, i.e. before carrying out the method of the present invention (in particular before obtaining the sample from the subject). However, the subject may or may not have had previous undiagnosed episodes of atrial fibrillation.

Preferably, the term “atrial fibrillation” refers to all types of atrial fibrillation. Accordingly, the term preferably encompasses paroxysmal, persistent or permanent atrial fibrillation.

In an embodiment of the present invention, however, the subject to be tested does not suffer from permanent atrial fibrillation. In this embodiment, the term “atrial fibrillation” only refers to paroxysmal and persistent atrial fibrillation.

In another embodiment of the present invention, however, the subject to be tested does not suffer from paroxysmal and permanent atrial fibrillation. In this embodiment, the term “atrial fibrillation” only refers to persistent atrial fibrillation.

The subject to be tested may or may not experience episodes of atrial fibrillation when the sample is obtained. Thus, in a preferred embodiment of the assessment of atrial fibrillation (such as in the diagnosis of atrial fibrillation), the subject does not experience episodes of Atrial Fibrillation when the sample is obtained. In this embodiment, the subject shall have a normal sinus rhythm when the sample is obtained (and shall be accordingly in sinus rhythm).

Thus, the diagnosis of atrial fibrillation is possible even in the (temporary) absence of atrial fibrillation. In accordance with the method of the present invention, the elevation of the biomarkers as referred to herein should be preserved after the episode of Atrial Fibrillation and, thus, provide a diagnosis of a subject who has suffered from Atrial Fibrillation. Preferably, the diagnosis of AF within about three days, within about one month, within about three months, or within about 6 months after carrying out the method of the present invention (or to be more precise after the sample has been obtained). In a preferred embodiment, the diagnosis of Atrial Fibrillation within about six months after the episode is feasible. In a preferred embodiment, the diagnosis of Atrial Fibrillation within about six months after the episode is feasible. Accordingly, the assessment of atrial fibrillation as referred to herein, in particular the diagnosis, the prediction of the risk or the differentiation as referred to herein in connection with the assessment of atrial fibrillation is preferably carried out after about three days, more preferably after about one month, even more preferably after about three month, and most preferably after about six months after the last episode of atrial fibrillation.

Consequently, is envisaged that is sample to be tested is preferably obtained after about three days, more preferably after about one month, even more preferably after about three month, and most preferably after about six months after the last episode of atrial fibrillation. Accordingly, the diagnosis of atrial fibrillation preferably also encompasses the diagnosis of episodes of atrial fibrillation that occurred preferably within about three days, more preferably within about three months, and most preferably within about six months before the sample was obtained.

However, it is also envisaged that the subject experiences episodes of atrial fibrillation when the sample is obtained (e.g. with respect to the prediction of stroke).

The term “sample” refers to a sample of a body fluid, to a sample of separated cells or to a sample from a tissue or an organ. Samples of body fluids can be obtained by well-known techniques and include, samples of blood, plasma, serum, urine, lymphatic fluid, sputum, ascites, or any other bodily secretion or derivative thereof. Tissue or organ samples may be obtained from any tissue or organ by, e.g., biopsy. Separated cells may be obtained from the body fluids or the tissues or organs by separating techniques such as centrifugation or cell sorting. E.g., cell-, tissue- or organ samples may be obtained from those cells, tissues or organs which express or produce the biomarker. The sample may be frozen, fresh, fixed (e.g. formalin fixed), centrifuged, and/or embedded (e.g. paraffin embedded), etc. The cell sample can, of course, be subjected to a variety of well-known post-collection preparative and storage techniques (e.g., nucleic acid and/or protein extraction, fixation, storage, freezing, ultrafiltration, concentration, evaporation, centrifugation, etc.) prior to assessing the amount of the biomarker (s) in the sample.

In a preferred embodiment of the present invention, the sample is a blood (i.e. whole blood), serum or plasma sample. Serum is the liquid fraction of whole blood that is obtained after the blood is allowed to clot. For obtaining the serum, the clot is removed by centrifugation and the supernatant is collected. Plasma is the acellular fluid portion of blood. For obtaining a plasma sample, whole blood is collected in anticoagulant-treated tubes (e.g. citrate-treated or EDTA-treated tubes). Cells are removed from the sample by centrifugation and the supernatant (i.e. the plasma sample) is obtained.

As set forth above, the subject may be in sinus rhythm or may suffer from an episode of AF rhythm at the time at which the sample is obtained. BMP10-type peptides are well known in the art. Preferred BMP10-types peptide are e.g. disclosed in Susan-Resiga et al. (J Biol Chem. 2011 Jul. 1; 286(26):22785-94) which herewith is incorporated by reference in its entirety (see e.g. FIG. 3A of Susan-Resiga et al., or US 2012/0213782).

In an embodiment, the BMP10-type peptide is unprocessed preproBMP10. In another embodiment, the BMP10-type peptide is the propeptide proBMP10. This marker comprises the N-terminal prosegement and BMP10. In another embodiment, the BMP10-type peptide is the N-terminal prosegment of BMP10 (N-terminal proBMP10). In another embodiment, the BMP10-type peptide is BMP10.

In an embodiment, the BMP10-type peptide is part of a homo- or heterodimeric complex.

Human preproBMP10 (i.e. unprocessed preproBMP10) has a length of 424 amino acids. The amino acid sequence of human preproBMP10 is e.g. shown in SEQ ID NO: 1 or in FIG. 3 of US 2012/0213782 which herewith is incorporated by reference in its entirety. Further, the amino acid sequence of preproBMP10 can be assessed via Uniprot (see sequence under accession number 095393-1). Human preproBMP10 comprises a short signal peptide (amino acids 1 to 21) which is enzymatically cleaved off to release proBMP10. Accordingly, human proBMP10 comprises amino acids 22 to 424 of human preproBMP10 (i.e. of the polypeptide having a sequence shown in SEQ ID NO 1). Human proBMP10 is further cleaved into an N-terminal prosegment of BMP10 and (non-glycosylated) BMP10 which is the active form. The N-terminal prosegment of BMP10 comprises amino acids 22 to 316 of the polypeptide having a sequence shown in SEQ ID NO 1 (i.e. of human preproBMP10). BMP10 comprises amino acids 317 to 424 of the polypeptide having a sequence shown in SEQ ID NO 1.

The preferred BMP10-type peptides are BMP10 and N-terminal proBMP10. After cleavage of proBMP10, BMP10 and N-terminal proBMP10 remain in structural proximity forming homo- or hetero-dimers of BMP10 or in combination with other BMP-family proteins (Yadin et al., CYTOGFR 2016, 27 (2016) 13-34). The dimerization occurs by formation of Cys-Cys bridge or strong adhesion in the C-terminal peptides of both binding partners. Thus, an architecture consisting of two subunits is formed.

Since proBMP10 is cleaved into BMP10 and the N-terminal prosegment in equimolar proportions, the amount of BMP10 reflects the amount of the N-terminal prosegment. Thus, the amount of BMP10 can be determined by determining the amount of the N-terminal prosegment and vice versa.

Preferably, the amount of the BMP10-type peptide is determined by using one or more antibodies (or antigen-binding fragments thereof) which specifically bind to the BMP10-type peptide.

For example, one or more antibodies which specifically bind to the N-terminal prosegment ofBMP10 could be used. Since such antibodies (or fragments) would also bind to proBMP10 and preproBMP10, the sum of the amounts of the N-terminal prosegment of BMP10, proBMP10 and preproBMP10 is determined in step a) of the methods of the present invention. Accordingly, the expression "determining the amount of the N-terminal prosegment of BMP10" also shall mean "determining the sum of the amounts of the N-terminal prosegment of BMP10, proBMP10 and preproBMP10".

Structural prediction based on findings from other BMP-type proteins as e.g. BMP9 show that BMP10 remains in a complex with proBMP10, thus detection of N-term prosegement also reflects the amount of BMP10.

For example, one or more antibodies which specifically bind to BMP10 could be used. Since such antibodies (or fragments) would also bind to proBMP10 and preproBMP10, the sum of the amounts of the BMP10, proBMP10 and preproBMP10 is determined in step a) of the methods of the present invention. Accordingly, the expression "determining the amount of BMP10" also shall mean "determining the sum of the amounts of BMP10, proBMP10 and preproBMP10".

Structural prediction based on findings from other BMP-type proteins as e.g. BMP9 show that BMP10 remains in a complex with proBMP10, thus detection of BMP10 also reflects the amount of N-terminal prosegment.

Further, it is envisaged to determine the sum of the amounts of all four BMP10-type peptides as referred to above, i.e. of BMP10, the N-terminal prosegment of BMP10, proBMP10 and preproBMP10.

Accordingly, the following amounts of BMP10-type peptides can be determined in accordance with the present invention:

- the amount of BMP10
- the amount of the N-terminal prosegment of BMP10
- the amount of proBMP10
- the amount of preproBMP10
- the sum of the amounts of BMP10, proBMP10 and preproBMP10
- the sum of the amounts of the N-terminal prosegment of BMP10, proBMP10 and preproBMP10, or
- the sum of the amounts of BMP10, the N-terminal prosegment of BMP10, proBMP10 and preproBMP10

The term "natriuretic peptide" comprises atrial natriuretic peptide (ANP)-type and brain natriuretic peptide (BNP)-type peptides. Thus, natriuretic peptides according to the present invention comprise ANP-type and BNP-type peptides and variants thereof (see, e.g., Bonow R O. et al., Circulation 1996; 93: 1946-1950).

ANP-type peptides comprise pre-proANP, proANP, NT-proANP, and ANP.

BNP-type peptides comprise pre-proBNP, proBNP, NT-proBNP, and BNP.

The pre-pro peptide (134 amino acids in the case of pre-proBNP) comprises a short signal peptide, which is enzymatically cleaved off to release the pro peptide (108 amino acids in the case of proBNP). The pro peptide is further cleaved into an N-terminal pro peptide (NTpro peptide, 76 amino acids in case ofNT-proBNP) and the active hormone (32 amino acids in the case of BNP, 28 amino acids in the case of ANP).

Preferred natriuretic peptides according to the present invention are NT-proANP, ANP, NT-proBNP, BNP. ANP and BNP are the active hormones and have a shorter half-life than their respective inactive counterparts, NT-proANP and NT-proBNP. BNP is metabolized in the blood, whereas NT-proBNP circulates in the blood as an intact molecule and as such is eliminated renally.

The most preferred natriuretic peptides according to the present invention are NT-proBNP and BNP, in particular NT-proBNP. As briefly discussed above, the human NT-proBNP as referred to in accordance with the present invention is a polypeptide comprising, preferably, 76 amino acids in length corresponding to the N-terminal portion of the human NT-proBNP molecule. The structure of the human BNP and NT-proBNP has been described already in detail in the prior art, e.g., WO 02/089657, WO 02/083913, and Bonow R O. Et al., New Insights into the cardiac natriuretic peptides. Circulation 1996; 93: 1946-1950. Preferably, human NT-proBNP as used herein is human NT-proBNP as disclosed in EP 0 648 228 B1.

The term "FABP-3" as used herein refers to the fatty acid binding protein 3. FABP-3 is also known as heart fatty acid binding protein or heart type fatty acid binding protein (abbreviated H-FABP). Preferably, the term also includes variants of FABP-3. FABP-3 as used herein, preferably, relates to human FABP-3. The DNA sequence of the polypeptide encoding the human FABP-3 polypeptide as well the protein sequence of human FABP-3 is well known in the art and was first described by Peeters et al. (Biochem. J. 276 (Pt 1), 203-207 (1991)). Moreover, the sequence of human H-FABP can be found, preferably, in Genbank entry U57623.1 (cDNA sequence) and AAB02555.1 (protein sequence). The major physiological function of FABP is thought to be the transport of free fatty acids, see e.g. Storch et al., Biochem. Biophys. Acta. 1486 (2000), 28-44. Other names for FABP-3 and H-FABP are: FABP-11 (fatty acid binding protein 11), M-FABP (muscle fatty acid-binding protein), MDGI (mammary-derived growth inhibitor), and O-FABP.

The biomarker endothelial cell specific molecule 1 (abbreviated ESM-1) is well known in the art. The biomarker is frequently also referred to as endocan. ESM-1 is a secreted protein which is mainly expressed in the endothelial cells in human lung and kidney tissues. Public domain data suggest expression also in thyroid, lung and kidney, but also in heart tissue, see. e.g. the entry for ESM-1 in the Protein Atlas database (Uhl6n M. et al., Science 2015; 347(6220): 1260419). The expression of this gene is regulated by cytokines. ESM-1 is a proteoglycan composed of a 20 kDa mature polypeptide and a 30 kDa O-linked glycan chain (Bechard D et al., J Biol Chem 2001; 276(51):48341-48349). In a preferred embodiment of the present invention, the amount of the human ESM-1 polypeptide is determined in a sample from the subject. The sequence of the human ESM-1 polypeptide is well known in the art (see e.g. Lassale P. et al., J. Biol. Chem. 1996; 271:20458-20464 and can be e.g. assessed via Uniprot database, see entry Q9NQ30 (ESMi_HUMAN). Two isoforms of ESM-1 are produced by alternative splicing, isoform 1 (having the Uniprot identifier Q9NQ30-1) and isoform 2 (having the Uniprot identifier Q9NQ30-2). Isoform 1 has length of 184 amino acids. In isoform 2, amino acids 101 to 150 of isoform 1 are missing. Amino acids 1 to 19 form the signal peptide (which might be cleaved off).

In a preferred embodiment, the amount of isoform 1 of the ESM-1 polypeptide is determined, i.e. isoform 1 having a sequence as shown under UniProt accession number Q9NQ30-1.

In another preferred embodiment, the amount of isoform 2 of the ESM-1 polypeptide is determined, i.e. isoform 2 having a sequence as shown under UniProt accession number Q9NQ30-2.

In another preferred embodiment, the amount of isoform-1 and isoform 2 of the ESM-1 polypeptide is determined, i.e. total ESM-1.

For example, the amount of ESM-1 could be determined with a monoclonal antibody (such as a mouse antibody) against amino acids 85 to 184 of the ESM-1 polypeptide and/or with a goat polyclonal antibody.

The biomarker Angiopoietin-2 (abbreviated "Ang-2", frequently also referred to as ANGPT2) is well known in the art. It is a naturally occurring antagonist for both Ang-1 and TIE2 (see e.g. Maisonpierre et al., Science 277 (1997) 55-60). The protein can induce tyrosine phosphorylation of TEK/TIE2 in the absence of ANG-1. In the absence of angiogenic inducers, such as VEGF, ANG2-mediated loosening of cell-matrix contacts may induce endothelial cell apoptosis with consequent vascular regression. In concert with VEGF, it may facilitate endothelial cell migration and proliferation, thus serving as a permissive angiogenic signal. The sequence of human Angiopoietin is well known in the art. Uniprot lists three isoforms of Angiopoietin-2: Isoform 1 (Uniprot identifier: O15123-1), Isoform 2 (identifier: O15123-2) and Isoform 3 (O15123-3). In a preferred embodiment, the total amount of Angiopoietin-2 is determined. The total amount is preferably the sum of the amounts of complexed and free Angiopoietin-2.

The term "determining" the amount of a biomarker as referred to herein (such as the BMP10-type peptide or the natriuretic peptide) refers to the quantification of the biomarker, e.g. to measuring the level of the biomarker in the sample, employing appropriate methods of detection described elsewhere herein. The terms "measuring" and "determining" are used herein interchangeably.

In an embodiment, the amount of a biomarker is determined by contacting the sample with an agent that specifically binds to the biomarker, thereby forming a complex between the agent and said biomarker, detecting the amount of complex formed, and thereby measuring the amount of said biomarker.

The biomarkers as referred to herein (such as the BMP10-type peptide) can be detected using methods generally known in the art. Methods of detection generally encompass methods to quantify the amount of a biomarker in the sample (quantitative method). It is generally known to the skilled artisan which of the following methods are suitable for qualitative and/or for quantitative detection of a biomarker. Samples can be conveniently assayed for, e.g., proteins using Westerns and immunoassays, like ELISAs, RIAs, fluorescence- and luminescence-based immunoassays and proximity extension assays, which are commercially available. Further suitable methods to detect biomarkers include measuring a physical or chemical property specific for the peptide or polypeptide such as its precise molecular mass or NMR spectrum. Said methods comprise, e.g., biosensors, optical devices coupled to immunoassays, biochips, analytical devices such as mass-spectrometers, NMR-analyzers, or chromatography devices. Further, methods include microplate ELISA-based methods, fully-automated or robotic immunoassays (available for example on Elecsys™ analyzers), CBA (an enzymatic Cobalt Binding Assay, available for example on Roche-Hitachi™ analyzers), and latex agglutination assays (available for example on Roche-Hitachi™ analyzers).

For the detection of biomarker proteins as referred to herein a wide range of immunoassay techniques using such an assay format are available, see, e.g., U.S. Pat. Nos. 4,016,043, 4,424,279, and 4,018,653. These include both single-site and two-site or "sandwich" assays of the non-competitive types, as well as in the traditional competitive binding assays. These assays also include direct binding of a labeled antibody to a target biomarker.

Methods employing electrochemiluminescent labels are well-known. Such methods make use of the ability of special metal complexes to achieve, by means of oxidation, an excited state from which they decay to ground state, emitting electrochemiluminescence. For review see Richter, M. M., Chem. Rev. 2004; 104: 3003-3036.

In an embodiment, the detection antibody (or an antigen-binding fragment thereof) to be used for measuring the amount of a biomarker is ruthenylated or iridinylated. Accordingly, the antibody (or an antigen-binding fragment thereof) shall comprise a ruthenium label. In an embodiment, said ruthenium label is a bipyridine-ruthenium(II) complex. Or the antibody (or an antigen-binding fragment thereof) shall comprise an iridium label. In an embodiment, said iridium label is a complex as disclosed in WO 2012/107419.

In an embodiment of the sandwich assay for the determination of the BMP10-type peptide, the assay comprises a biotinylated first monoclonal antibody that specifically binds a BMP10-type peptide (as capture antibody) and a ruthenylated F(ab')2-fragment of a second monoclonal antibody that specifically binds a BMP10-type peptide as detection antibody). The two antibodies form sandwich immunoassay complexes with the BMP10-type peptide in the sample.

In an embodiment of the sandwich assay for the determination of the natriuretic peptide, the assay comprises a biotinylated first monoclonal antibody that specifically binds the natriuretic peptide (as capture antibody) and a ruthenylated F(ab')2-fragment of a second monoclonal antibody that specifically binds the natriuretic peptide as detection antibody). The two antibodies form sandwich immunoassay complexes with the natriuretic peptide in the sample.

Measuring the amount of a polypeptide (such as a BMP10-type peptide or the natriuretic peptide) may, preferably, comprise the steps of (a) contacting the polypeptide with an agent that specifically binds said polypeptide, (b) (optionally) removing non-bound agent, (c) measuring the amount of bound binding agent, i.e. the complex of the agent formed in step (a). According to a preferred embodiment, said steps of contacting, removing and measuring may be performed by an analyzer unit. According to some embodiments, said steps may be performed by a single analyzer unit of said system or by more than one analyzer unit in operable communication with each other. For example, according to a specific embodiment, said system disclosed herein may include a first analyzer unit for performing said steps of contacting and removing and a second analyzer unit, operably connected to said first analyzer unit by a transport unit (for example, a robotic arm), which performs said step of measuring.

The agent which specifically binds the biomarker (herein also referred to as "binding agent") may be coupled covalently or non-covalently to a label allowing detection and measurement of the bound agent. Labeling may be done by direct or indirect methods. Direct labeling involves coupling of the label directly (covalently or non-covalently) to the binding agent. Indirect labeling involves binding (covalently or non-covalently) of a secondary binding agent to the first binding agent. The secondary binding agent should specifically bind to the first binding agent. Said secondary binding agent may be coupled with a suitable label and/or be the target (receptor) of a tertiary binding agent binding to the secondary binding agent. Suitable secondary and higher order binding agents may include antibodies, secondary antibodies, and the well-known streptavidin-biotin system (Vector Laboratories, Inc.). The binding agent or substrate may also be "tagged" with one or more tags as known in the art. Such tags may then be targets for higher order binding agents. Suitable tags include biotin, digoxygenin, His-Tag, Glutathion-S-Transferase, FLAG, GFP, myc-tag, influenza A virus haemagglutinin (HA), maltose binding protein, and the like. In the case of a peptide or polypeptide, the tag is preferably at the N-terminus and/or C-terminus. Suitable labels are any labels detectable by an appropriate detection method. Typical labels include gold particles, latex beads, acridan ester, luminol, ruthenium complexes, iridium complexes, enzymatically active labels, radioactive labels, magnetic labels ("e.g. magnetic beads", including paramagnetic and superparamagnetic labels), and fluorescent labels. Enzymatically active labels include e.g. horseradish peroxidase, alkaline phosphatase, beta-Galactosidase, Luciferase, and derivatives thereof. Suitable substrates for detection include di-amino-benzidine (DAB), 3,3'-5,5'-tetramethylbenzidine, NBT-BCIP (4-nitro blue tetrazolium chloride and 5-bromo-4-chloro-3-indolyl-phosphate, avail-able as ready-made stock solution from Roche Diagnostics), CDP-Star™ (Amersham Bio-sciences), ECF™ (Amersham Biosciences). A suitable enzyme-substrate combination may result in a colored reaction product, fluorescence or chemoluminescence, which can be determined according to methods known in the art (e.g. using a light-sensitive film or a suitable camera system). As for measuring the enzymatic reaction, the criteria given above apply analogously. Typical fluorescent labels include fluorescent proteins (such as GFP and its derivatives), Cy3, Cy5, Texas Red, Fluorescein, and the Alexa dyes (e.g. Alexa 568). Further fluorescent labels are available e.g. from Molecular Probes (Oregon). Also the use of quantum dots as fluorescent labels is contemplated. A radioactive label can be detected by any method known and appropriate, e.g. a light-sensitive film or a phosphor imager.

The amount of a polypeptide may be, also preferably, determined as follows: (a) contacting a solid support comprising a binding agent for the polypeptide as described elsewhere herein with a sample comprising the peptide or polypeptide and (b) measuring the amount of peptide or polypeptide which is bound to the support. Materials for manufacturing supports are well-known in the art and include, inter alia, commercially available column materials, polystyrene beads, latex beads, magnetic beads, colloid metal particles, glass and/or silicon chips and surfaces, nitrocellulose strips, membranes, sheets, duracytes, wells and walls of reaction trays, plastic tubes etc.

In yet an aspect the sample is removed from the complex formed between the binding agent and the at least one marker prior to the measurement of the amount of formed complex. Accordingly, in an aspect, the binding agent may be immobilized on a solid support. In yet an aspect, the sample can be removed from the formed complex on the solid support by applying a washing solution.

"Sandwich assays" are among the most useful and commonly used assays encompassing a number of variations of the sandwich assay technique. Briefly, in a typical assay, an unlabeled (capture) binding agent is immobilized or can be immobilized on a solid substrate, and the sample to be tested is brought into contact with the capture binding agent. After a suitable period of incubation, for a period of time sufficient to allow formation of a binding agent-biomarker complex, a second (detection) binding agent labeled with a reporter molecule capable of producing a detectable signal is then added and incubated, allowing time sufficient for the formation of another complex of binding agent-biomarker-labeled binding agent. Any unreacted material may be washed away, and the presence of the biomarker is determined by observation of a signal produced by the reporter molecule bound to the detection binding agent. The results may either be qualitative, by simple observation of a visible signal, or may be quantitated by comparison with a control sample containing known amounts of biomarker.

The incubation steps of a typical sandwich assays can be varied as required and appropriate. Such variations include for example simultaneous incubations, in which two or more of binding agent and biomarker are co-incubated. For example, both, the sample to be analyzed and a labeled binding agent are added simultaneously to an immobilized capture binding agent. It is also possible to first incubate the sample to be analyzed and a labeled binding agent and to thereafter add an antibody bound to a solid phase or capable of binding to a solid phase.

The formed complex between a specific binding agent and the biomarker shall be proportional to the amount of the biomarker present in the sample. It will be understood that the specificity and/or sensitivity of the binding agent to be applied defines the degree of proportion of at least one marker comprised in the sample which is capable of being specifically bound. Further details on how the measurement can be carried out are also found elsewhere herein. The amount of formed complex shall be transformed into an amount of the biomarker reflecting the amount indeed present in the sample.

The terms "binding agent", "specific binding agent", "analyte-specific binding agent", "detection agent" and "agent that specifically binds to a biomarker" are used interchangeably herein. Preferably it relates to an agent that comprises a binding moiety which specifically binds the corresponding biomarker. Examples of "binding agents", "detection agents", "agents" are a nucleic acid probe, nucleic acid primer, DNA molecule, RNA molecule, aptamer, antibody, antibody fragment, peptide, peptide nucleic acid (PNA) or chemical compound. A preferred agent is an antibody which specifically binds to the biomarker to be determined. The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity (i.e. antigen-binding fragments thereof). Preferably, the antibody is a polyclonal antibody (or an antigen-binding fragment therefrom). More preferably, the antibody is a monoclonal antibody (or an antigen binding fragment therefore. Moreover, as described elsewhere herein, it is envisaged that two monoclonal antibodies are used that bind at different positions of the BMP10-type peptide (in a sandwich immunoassay). Thus, at least one antibody is used for the determination of the amount of the BMP10-type peptide.

In an embodiment, the at least one antibody is a mouse monoclonal antibody. In another embodiment, the at least one antibody is a rabbit monoclonal antibody. In a further embodiment, the antibody is goat polyclonal antibody. In an even further embodiment, the antibody is a sheep polyclonal antibody.

The term "specific binding" or "specifically bind" refers to a binding reaction wherein binding pair molecules exhibit a binding to each other under conditions where they do not significantly bind to other molecules. The term "specific binding" or "specifically binds", when referring to a protein or peptide as biomarker, preferably refers to a binding reaction wherein a binding agent binds to the corresponding biomarker with an affinity ("association constant" $K_a$) of at least $10^7$ $M^{-1}$. The term "specific binding" or "specifically binds" preferably refers to an affinity of at least $10^8$ $M^{-1}$ or even more preferred of at least $10^9$ $M^{-1}$ for its target molecule. The term "specific" or "specifically" is used to indicate that other molecules present in the sample do not significantly bind to the binding agent specific for the target molecule.

The term "amount" as used herein encompasses the absolute amount of a biomarker as referred to herein (such as the BMP10-type peptide or the natriuretic peptide), the relative amount or concentration of the said biomarker as well as any value or parameter which correlates thereto or can be derived therefrom. Such values or parameters comprise intensity signal values from all specific physical or chemical properties obtained from the said peptides by direct measurements, e.g., intensity values in mass spectra or NMR spectra. Moreover, encompassed are all values or parameters which are obtained by indirect measurements specified elsewhere in this description, e.g., response amounts determined from biological read out systems in response to the peptides or intensity signals obtained from specifically bound ligands. It is to be understood that values correlating to the aforementioned amounts or parameters can also be obtained by all standard mathematical operations.

The term "comparing" as used herein refers to comparing the amount of the biomarker (such as the BMP10-type peptide and the natriuretic peptide such as NT-proBNP or BNP) in the sample from the subject with the reference amount of the biomarker specified elsewhere in this description. It is to be understood that comparing as used herein usually refers to a comparison of corresponding parameters or values, e.g., an absolute amount is compared to an absolute reference amount while a concentration is compared to a reference concentration or an intensity signal obtained from the biomarker in a sample is compared to the same type of intensity signal obtained from a first sample. The comparison may be carried out manually or computer-assisted. Thus, the comparison may be carried out by a computing device. The value of the determined or detected amount of the biomarker in the sample from the subject and the reference amount can be, e.g., compared to each other and the said comparison can be automatically carried out by a computer program executing an algorithm for the comparison. The computer program carrying out the said evaluation will provide the desired assessment in a suitable output format. For a computer-assisted comparison, the value of the determined amount may be compared to values corresponding to suitable references which are stored in a database by a computer program. The computer program may further evaluate the result of the comparison, i.e. automatically provide the desired assessment in a suitable output format. For a computer-assisted comparison, the value of the determined amount may be compared to values corresponding to suitable references which are stored in a database by a computer program. The computer program may further evaluate the result of the comparison, i.e. automatically provides the desired assessment in a suitable output format.

In accordance with the present invention, the amount of a BMP10-type peptide and optionally the amount of the at least one further biomarker (such as the natriuretic peptide) shall be compared to a reference. The reference is preferably a reference amount. The term "reference amount" is well understood by the skilled person. It is to be understood that the reference amount shall allow for the herein described assessment of atrial fibrillation. E.g., in connection with the method for diagnosing atrial fibrillation, the reference amount preferably refers to an amount which allows for allocation of a subject into either (i) the group of subjects suffering from atrial fibrillation or (ii) the group of subjects not suffering from atrial fibrillation. A suitable reference amount may be determined from a first sample to be analyzed together, i.e. simultaneously or subsequently, with the test sample.

It is to be understood that the amount of the BMP10-type peptide is compared to a reference amount for the BMP10-type peptide, whereas the amount of the at least one further biomarker (such as the natriuretic peptide) is compared to a reference amount for said at least one at least one further biomarker (such as the natriuretic peptide). If the amounts of two markers or more are determined, it is also envisaged that a combined score is calculated based on the amounts the two or more marker (such as the amount of the BMP10-type peptide and the amount of the natriuretic peptide). In a subsequent step, the score is compared to a reference score.

Reference amounts can, in principle, be calculated for a cohort of subjects as specified above based on the average or mean values for a given biomarker by applying standard methods of statistics. In particular, accuracy of a test such as a method aiming to diagnose an event, or not, is best described by its receiver-operating characteristics (ROC) (see especially Zweig M H. et al., Clin. Chem. 1993; 39:561-577). The ROC graph is a plot of all the sensitivity versus specificity pairs resulting from continuously varying the decision threshold over the entire range of data observed. The clinical performance of a diagnostic method depends on its accuracy, i.e. its ability to correctly allocate subjects to a certain prognosis or diagnosis. The ROC plot indicates the overlap between the two distributions by plotting the sensitivity versus 1—specificity for the complete range of thresholds suitable for making a distinction. On the y-axis is sensitivity, or the true-positive fraction, which is defined as the ratio of number of true-positive test results to the product of number of true-positive and number of false-negative test results. It is calculated solely from the affected subgroup. On the x-axis is the false-positive fraction, or 1—specificity, which is defined as the ratio of number of false-positive results to the product of number of true-negative and number of false-positive results. It is an index of specificity and is calculated entirely from the unaffected subgroup. Because the true- and false-positive fractions are calculated entirely separately, by using the test results from two different subgroups, the ROC plot is independent of the prevalence of the event in the cohort. Each point on the ROC plot represents a sensitivity/1—specificity pair corresponding to a particular decision threshold. A test with perfect discrimination (no overlap in the two distributions of results) has an ROC plot that passes through the upper left corner, where the true-positive fraction is 1.0, or 100% (perfect sensitivity), and the false-positive fraction is 0 (perfect specificity). The theoretical plot for a test with no discrimination (identical distributions of results for the two groups) is a 45 diagonal line from the lower left corner to the upper right corner. Most plots fall in between these two extremes. If the ROC plot falls completely below the 45° diagonal, this is easily remedied by reversing the criterion for "positivity" from "greater than" to "less than" or vice versa. Qualitatively, the closer the plot is to the upper left corner, the higher the overall accuracy of the test. Dependent on a desired confidence interval, a threshold can be derived from the ROC curve allowing for the diagnosis for a given event with a proper balance of sensitivity and specificity, respectively. Accordingly, the reference to be used for the method of the present invention, i.e. a threshold which allows to assess atrial fibrillation can be generated, preferably, by establishing a ROC for said cohort as described above and deriving a threshold amount therefrom. Dependent on a desired sensitivity and specificity for a diagnostic method, the ROC plot allows deriving a suitable threshold. It will be understood that an optimal sensitivity is desired for e.g. excluding a subject from suffering from atrial fibrillation (i.e. a rule out) whereas an optimal specificity is envisaged for a subject to be assessed as suffering from atrial fibrillation (i.e. a rule in). In an embodiment, the method of the present invention allows for the prediction that a subject is at risk of an adverse event associated with atrial fibrillation such as the occurrence or recurrence of Atrial Fibrillation and/or stroke.

In a preferred embodiment, the term "reference amount" herein refers to a predetermined value. Said predetermined value shall allow for assessing atrial fibrillation, and thus for diagnosing atrial fibrillation, for differentiating between paroxysmal and persistent atrial fibrillation, for prediction the risk of an adverse event associated with atrial fibrillation, for identifying a subject who shall be subjected to electrocardiography (ECG), or for the assessment of a therapy for atrial fibrillation. It is to be understood that the reference amount may differ based on the type of assessment. E.g., the reference amount for the BMP10-type peptide for the differentiation of AF will be usually higher than the reference amount for the diagnosis of AF. However, this will be taken into account by the skilled person.

As set forth above, the term "assessing atrial fibrillation" preferably refers to the diagnosis of atrial fibrillation, the differentiation between paroxysmal and persistent atrial fibrillation, the prediction of a risk of an adverse event associated with atrial fibrillation, to the identification of a subject who shall be subjected to electrocardiography (ECG), or the assessment of a therapy for atrial fibrillation. In the following, these embodiments of the method of the present invention will be described in more detail. The definitions above apply accordingly.

Method for Diagnosing Atrial Fibrillation

The term "diagnosing" as used herein means assessing whether a subject as referred to in accordance with the method of the present invention suffers from atrial fibrillation (AF), or not. In a preferred embodiment, it is diagnosed that a subject suffers from paroxysmal AF. In an alternative embodiment, it is diagnosed that a subject does not suffer from AF.

In accordance with the present invention, all types of AF can be diagnosed. Thus, the atrial fibrillation may be paroxysmal, persistent or permanent AF. Preferably, paroxysmal or persistent atrial fibrillation is diagnosed, in particular in a subject not suffering from permanent AF.

The actual diagnosis whether a subject suffers from AF, or not may comprise further steps such as the confirmation of a diagnosis (e.g. by ECG such as Holter-ECG). Thus, the present invention allows for assessing the likelihood that a patient suffers from atrial fibrillation. A subject who has an amount of BMP10 above the reference amount is likely to suffer from atrial fibrillation, whereas a subject who has an amount of BMP10 below the reference amount is not likely to suffer from atrial fibrillation. Accordingly, the term "diagnosing" in the context of the present invention also encompasses aiding the physician to assess whether a subject suffers from atrial fibrillation, or not.

Preferably, an amount of the BMP10-type peptide (and optionally an amount of the at least one further biomarker such as ESM-1, Ang-2, FABP-3 and/or the natriuretic peptide) in the sample from a test subject which is (are) increased as compared to the reference amount (or to the reference amounts) is indicative for a subject suffering from atrial fibrillation, and/or an amount of the BMP10-type peptide (and optionally an amount of the at least one further biomarker such as ESM-1, Ang-2, FABP-3 and/or the natriuretic peptide) in the sample from a subject which is (are) decreased as compared to the reference amount (or the reference amounts) is indicative for a subject not suffering from atrial fibrillation.

In a preferred embodiment, the reference amount, i.e. the reference amount for the BMP10-type peptide and, if determined, the reference amount for the at least one further biomarker, shall allow for differentiating between a subject suffering from atrial fibrillation and a subject not suffering from atrial fibrillation. Preferably, said reference amount is a predetermined value.

In an embodiment, the method of the present invention allows for the diagnosis of a subject suffering from atrial fibrillation. Preferably, the subject is suffering from AF, if the amount of the BMP10-type peptide (and optionally an amount of the at least one further biomarker such as ESM-1, Ang-2, FABP-3 and/or the natriuretic peptide) is (are) above the reference amount. In an embodiment, the subject is suffering from AF, if the amount of the BMP10-type peptide is above a certain percentile (e.g. $99^{th}$ percentile) upper reference limit (URL) of a reference amount.

In an embodiment of the method of diagnosing atrial fibrillation, said method further comprises a step of recommending and/or initiating a therapy for atrial fibrillation based on the results of the diagnosis. Preferably, a therapy is recommended or initiated if it is diagnosed that the subject suffers from AF. Preferred therapies for atrial fibrillation are disclosed elsewhere herein (such as anticoagulation therapies).

Method for Differentiating Between Paroxysmal and Persistent Atrial Fibrillation The term "differentiating" as used herein means to distinguish between paroxysmal and persistent atrial fibrillation in a subject. The term as used herein, preferably, includes differentially diagnosing paroxysmal and persistent atrial fibrillation in a subject. Thus, the method of the present invention allows for assessing whether a subject with atrial fibrillation suffers from paroxysmal atrial fibrillation or persistent atrial fibrillation. The actual differentiation may comprise further steps such as the confirmation of the differentiation. Thus, the term "differentiation" in the context of the present invention also encompasses aiding the physician to differentiate between paroxysmal and persistent AF.

Preferably, an amount of the BMP10-type peptide (and optionally an amount of the at least one further biomarker such as ESM-1, Ang-2, FABP-3 and/or the natriuretic peptide) in the sample from a subject which is (are) increased as compared to the reference amount (or to the reference amounts) is indicative for a subject suffering from persistent atrial fibrillation and/or an amount of the BMP10-type peptide (and optionally an amount of the at least one further biomarker such as ESM-1, Ang-2, FABP-3 and/or the natriuretic peptide) in the sample from a subject which is (are) decreased as compared to a reference amount (or to the reference amounts) is indicative for a subject suffering from paroxysmal atrial fibrillation. In both AF types (paroxysmal and persistent), the amount of the BMP10-type peptide is increased as compared to the reference amount of non-AF subjects.

In a preferred embodiment, the reference amount(s) shall allow for differentiating between a subject suffering from paroxysmal atrial fibrillation and a subject suffering from persistent atrial fibrillation. Preferably, said reference amount is a predetermined value.

In an embodiment of the above method of differentiating between paroxysmal and persistent atrial fibrillation, the subject does not suffer from permanent atrial fibrillation.

Method for Predicting the Risk a Risk of an Adverse Event Associated with Atrial Fibrillation The method of the present invention also contemplates a method for predicting the risk of an adverse event.

In an embodiment, the risk of an adverse event as set forth herein can be the prediction of any adverse event associated with atrial fibrillation. Preferably, said adverse event is selected from recurrence of atrial fibrillation (such as the recurrence of atrial fibrillation after cardioversion) and stroke. Accordingly, the risk of a subject (who suffers from atrial fibrillation) to suffer in the future from an adverse event (such as stroke or recurrence of atrial fibrillation) shall be predicted.

Further, it is envisaged that said adverse event associated with atrial fibrillation is the occurrence of atrial fibrillation in a subject has no known history of atrial fibrillation.

In a particularly preferred embodiment, the risk of stroke is predicted.

Accordingly, the present invention method for predicting the risk of stroke in a subject, comprising the steps of

- a) determining the amount of a BMP10-type peptide in a sample from the subject, and
- b) comparing the amount of the BMP10-type peptide to a reference amount, whereby the risk of stroke is to be predicted.

In particular, the present invention relates to a method for predicting the risk of stroke in a subject, comprising the steps of

- (a) determining, in at least one sample from the subject, the amount of a BMP10-type peptide (Bone Morphogenic Protein 10) and, optionally, the amount of at least one further biomarker selected from the group consisting of a natriuretic peptide, ESM-1 (Endocan), Ang2 (Angiopoietin 2) and FABP-3 (Fatty acid binding protein 3), and
- (b) comparing the amount of the BMP10-type peptide to a reference amount for the BMP10-type peptide and, optionally, comparing the amount of the at least one further biomarker to a reference amount for said at least one further biomarker, whereby the risk of stroke is to be predicted.

Preferably, term "predicting the risk" as used herein refers to assessing the probability according to which the subject will suffer from an adverse event as referred to herein (e.g. of stroke). Typically, it is predicted whether a subject is at risk (and thus at elevated risk) or not at risk (and thus at reduced risk) of suffering from said adverse event. Accordingly, the method of the present invention allows for differentiating between a subject at risk and a subject not at risk of suffering from said adverse event. Further, it is envisaged that the method of the present invention allows for differentiating between a subject who is a reduced, average, or elevated risk.

As set forth above, the risk (and probability) of suffering from said adverse event within a certain time window shall be predicted. In a preferred embodiment of the present invention, the predictive window is a period of about three months, about six months, or, in particular, about one year. Thus, the short-term risk is predicted.

In another preferred embodiment, the predictive window is a period of about five years (e.g. for the prediction of stroke). Further, the predictive window might be a period of about six years (e.g. for the prediction of stroke). Alternatively, the predictive window may be about 10 years. Also, it is envisaged that the predictive window a period of 1 to 3 years. Thus, the risk to suffer from stroke within 1 to 3 year is predicted. Also, it is envisaged that the predictive window a period of 1 to 10 years. Thus, the risk to suffer from stroke within 1 to 10 years is predicted.

Preferably, said predictive window is calculated from the completion of the method of the present invention. More preferably, said predictive window is calculated from the time point at which the sample to be tested has been obtained. As will be understood by those skilled in the art, the prediction of a risk is usually not intended to be correct for 100% of the subjects. The term, however, requires that prediction can be made for a statistically significant portion of subjects in a proper and correct manner. Whether a portion is statistically significant can be determined without further ado by the person skilled in the art using various well known statistic evaluation tools, e.g., determination of confidence intervals, p-value determination, Student's t-test, Mann-Whitney test etc. Details are found in Dowdy and Wearden, Statistics for Research, John Wiley & Sons, New York 1983. Preferred confidence intervals are at least 90%, at least 95%, at least 97%, at least 98%, or at least 99%. The p-values are, preferably, 0.1, 0.05, 0.01, 0.005, or 0.0001.

In a preferred embodiment, the expression "predicting the risk of suffering from said adverse event" means that the subject to be analyzed by the method of the present invention is allocated either into the group of subjects being at risk of suffering from said adverse event, or into the group of subjects not being at risk of suffering from said adverse event (such as stroke). Thus, it is predicted whether the subject is at risk or not at risk of suffering from said adverse event. As used herein "a subject who is at risk of suffering from said adverse event", preferably has an elevated risk of suffering from said adverse event (preferably within the predictive window). Preferably, said risk is elevated as compared to the average risk in a cohort of subjects. As used herein, "a subject who is not at risk of suffering from said adverse event", preferably, has a reduced risk of suffering from said adverse event (preferably within the predictive window). Preferably, said risk is reduced as compared to the average risk in a cohort of subjects. A subject who is at risk of suffering from said adverse event preferably has a risk of suffering from said adverse event such as recurrence or occurrence of atrial fibrillation of at least 20% or more preferably of at least 30%, preferably, within a predictive window of about one year. A subject who is not at risk of suffering from said adverse event preferably has a risk of lower than 12%, more preferably of lower than 10% of suffering from said adverse event, preferably within a predictive window of one year.

With respect to the prediction of stroke, a subject who is at risk of suffering from said adverse event preferably has a risk of suffering from said adverse event of at least 10% or more preferably of at least 13%, preferably, within a predictive window of about five years, or in particular of about six years. A subject who is not at risk of suffering from said adverse event preferably has a risk of lower than 10%, more preferably of lower than 8%, or most preferably of lower than 5% of suffering from said adverse event, preferably within a predictive window of about five years, or in particular of about six years. The risk may be higher, if the subject does not receive anticoagulation therapy. This will be taken into account by the skilled person.

Preferably, an amount of the BMP10-type peptide (and optionally an amount of the at least one further biomarker such as ESM-1, Ang-2, FABP-3 and/or the natriuretic peptide) in the sample from a subject which is (are) increased as compared to the reference amount (or to the reference amounts) is indicative for a subject who is at risk of the adverse event associated with atrial fibrillation, and/or an amount of the BMP10-type peptide (and optionally an amount of the at least one further biomarker such as ESM-1, Ang-2, FABP-3 and/or the natriuretic peptide) in the sample from a subject which is decreased as compared to the reference amount (or to the reference amounts) is indicative for a subject who is not at risk the adverse event associated with atrial fibrillation.

In a preferred embodiment, the reference amount (or reference amounts) shall allow for differentiating between a subject who is at risk of an adverse event as referred to herein and a subject who is not at risk of said adverse event. Preferably, said reference amount is a predetermined value.

The adverse event to be predicted is preferably stroke. The term "stroke" is well known in the art. As used herein, the term, preferably, refers to ischemic stroke, in particular to cerebral ischemic stroke. A stroke which is predicted by the method of the present invention shall be caused by reduced blood flow to the brain or parts thereof which leads to an undersupply of oxygen to brain cells. In particular, the stroke leads to irreversible tissue damage due to brain cell death. Symptoms of stroke are well known in the art. E.g., stroke symptoms include sudden numbness or weakness of face, arm or leg, especially on one side of the body, sudden confusion, trouble speaking or understanding, sudden trouble seeing in one or both eyes, and sudden trouble walking, dizziness, loss of balance or coordination. Ischemic stroke may be caused by atherothrombosis or embolism of a major cerebral artery, by coagulation disorders or non-atheromatous vascular disease, or by cardiac ischemia which leads to a reduced overall blood flow. The ischemic stroke is preferably selected from the group consisting of atherothrombotic stroke, cardioembolic stroke and lacunar stroke. Preferably, the stroke to be predicted is an acute ischemic stroke, in particular cardioembolic stroke. A cardioembolic stroke (frequently also referred to as embolic or thromboembolic stroke) can be caused by atrial fibrillation.

Preferably, said stroke shall be associated with atrial fibrillation. More preferably, the stroke shall be caused by atrial fibrillation. However, it is also envisaged that the subject has no history of atrial fibrillation.

Preferably, a stroke is associated with atrial fibrillation, if there is a temporal relationship between the stroke and an episode of atrial fibrillation. More preferably, a stroke is associated with atrial fibrillation, if the stroke is caused by atrial fibrillation. Most preferably, a stroke is associated with atrial fibrillation, if the stroke can be caused by atrial fibrillation.

For example, a cardioembolic stroke (frequently also referred to as embolic or thromboembolic stroke) can be caused by atrial fibrillation. Preferably, a stroke associated with AF can be prevented by oral anticoagulation. Also preferably, the stroke is considered as associated with atrial fibrillation, if the subject to be tested suffers from atrial fibrillation and/or has a known history thereof. Also, in an embodiment, the stroke may be considered as being associated with atrial fibrillation, if the subject is suspected to suffer from atrial fibrillation.

The term "stroke" does, preferably, not include hemorrhagic stroke.

In a preferred embodiment of the aforementioned method of predicting an adverse event (such as stroke), the subject to be tested suffers from atrial fibrillation. More preferably, the subject has a known history of atrial fibrillation. In accordance with the method for predicting an adverse event, the subject preferably suffers from permanent atrial fibrillation, more preferably from persistent atrial fibrillation and most preferably from paroxysmal atrial fibrillation.

In an embodiment of the method of predicting an adverse event, the subject suffering from atrial fibrillation experiences episodes of atrial fibrillation when the sample is obtained. In another embodiment of the method of predicting an adverse event, the subject suffering from atrial fibrillation does not experiences episode of atrial fibrillation when the sample is obtained (and thus shall have a normal sinus rhythm). Further, the subject whose risk is to be predicted may be on anticoagulation therapy.

In another embodiment of the method of predicting an adverse event, the subject to be tested has no known history of atrial fibrillation. In particular, it is envisaged that the subject does not suffer from atrial fibrillation.

The method of the present invention may aid personalized medicine. In a preferred embodiment, the method for predicting the risk of stroke in a subject further comprises i) the step of recommending anticoagulation therapy, or ii) of recommending an intensification of anticoagulation therapy, if the subject has been identified to be at risk to suffer from stroke. In a preferred embodiment, the method for predicting the risk of stroke in a subject further comprises i) the step of initiating anticoagulation therapy, or ii) of intensifying anticoagulation therapy, if the subject has been identified to be at risk to suffer from stroke (by the method of the present invention).

If the test subject is on anticoagulation therapy, and if the subject has been identified not to be at risk to suffer from stroke (by the method of the present invention) the dosage of anticoagulation therapy may be reduced. Accordingly, a reduction of the dosage may be recommended. Be reducing the dosage, the risk to suffer from side effects (such as bleeding) may be reduced.

The term "recommending" as used herein means establishing a proposal for a therapy which could be applied to the subject. However, it is to be understood that applying the actual therapy whatsoever is not comprised by the term. The therapy to be recommended depends on the outcome of the provided by the method of the present invention.

In particular, the following applies:

If the subject to be tested does not receive anticoagulation therapy, the initiation of anticoagulation is recommended, if the subject has been identified to be at risk to suffer from stroke. Thus, anticoagulation therapy shall be initiated.

If the subject to be tested already receives anticoagulation therapy, the intensification of anticoagulation is recommended, if the subject has been identified to be at risk to suffer from stroke. Thus, anticoagulation therapy shall be intensified.

In a preferred embodiment, anticoagulation therapy is intensified by increasing the dosage of the anticoagulant, i.e. the dosage of the currently administered coagulant.

In a particularly preferred embodiment, anticoagulation therapy is intensified by increasing the replacing the currently administered anticoagulant with a more effective anticoagulant. Thus, a replacement of the anticoagulant is recommended.

Figure 4:
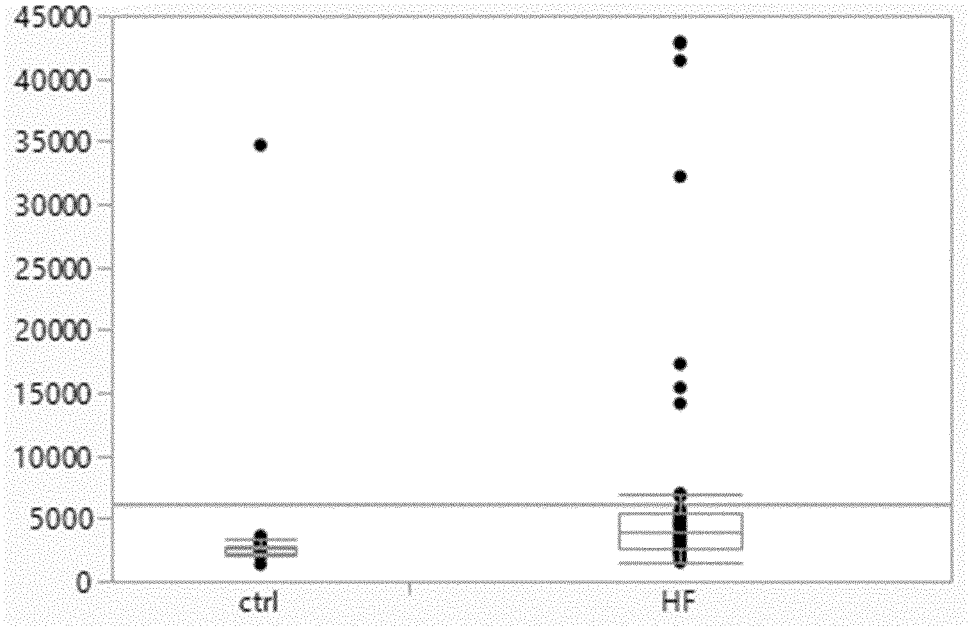

It has been described that better prevention in high risk patients is achieved with the oral anticoagulant apixaban versus the vitamin K antagonist warfarin as shown in Hijazi at al., The Lancet 2016 387, 2302-2311, (FIG. 4).

Thus, it is envisaged that the subject to be tested is a subject who is treated with a vitamin K antagonist such as warfarin or dicumarol. If the subject has been identified to be at risk to suffer from stroke (by the method of the present invention, it the replacement of the vitamin K antagonist with an oral anticoagulant, in particular dabigatran, rivaroxaban or apixaban is recommended. Accordingly, the therapy with the vitamin K antagonist is discontinued and therapy with an oral anticoagulant is initiated.

Method for Identifying a Subject Who Shall be Subjected to Electrocardiography (ECG)

In accordance with this embodiment of method of the present invention, it shall be assessed whether the subject to be tested with the biomarker shall be subjected to electrocardiography (ECG), i.e. to an electrocardiography assessment. Said assessment shall be carried for diagnosing, i.e. to detect the presence of absence of AF, in said subject.

The term "identifying a subject" as used herein preferably refers to using the information or data generated relating to the amount of BMP10 (and optionally the amount of the at least one further biomarker) in a sample of a subject to identify subject shall be subjected to ECG. The subject who is identified has an increased likelihood of suffering from AF. The ECG assessment is made as a confirmation.

Electrocardiography (abbreviated ECG) is the process of recording the electrical activity of the heart by suitable ECG. An ECG device records the electrical signals produced by the heart which spread throughout the body to the skin. The recording is of the electrical signal is achieved by contacting the skin of the test subject with electrodes comprised by the ECG device. The process of obtaining the recording is non-invasive and risk-free. The ECG is carried out for the diagnosis of atrial fibrillation, i.e. for the assessment of the presence of absence of atrial fibrillation in the test subject. In embodiment of the method of the present invention, the ECG device is a one-lead device (such as a one-lead handheld ECG-device). In another preferred embodiment the ECG device is a 12-lead ECG device such as a Holter monitor.

Preferably, an amount of the BMP10-type peptide (and optionally an amount of the at least one further biomarker such as ESM-1, Ang-2, FABP-3 and/or the natriuretic peptide) in the sample from a test subject which is (are) increased as compared to the reference amount (or to the reference amounts) is indicative for a subject who shall be subjected to ECG, and/or an amount of the BMP10-type peptide (and optionally an amount of the at least one further biomarker such as ESM-1, Ang-2, FABP-3 and/or the natriuretic peptide) in the sample from a subject which is (are) decreased as compared to the reference amount (or to the reference amounts) is indicative for a subject who shall not be subjected to ECG.

In a preferred embodiment, the reference amount shall allow for differentiating between a subject who shall be subjected to ECG and a subject who shall not be subjected to ECG. Preferably, said reference amount is a predetermined value.

In an embodiment of the aforementioned method, the method comprises identifying a subject who shall be subjected to electrocardiography, in particular, when the amount of the BMP10-type peptide (and optionally an amount of the at least one further biomarker such as ESM-1, Ang-2, FABP-3 and/or the natriuretic peptide) in the sample from the test subject is (are) increased as compared to the reference amount (or to the reference amounts), and subjecting the identified subject to electrocardiographv.

Method for the Assessment of a Therapy for Atrial Fibrillation

As used herein, the term "assessing a therapy for atrial fibrillation", preferably refers to the assessment of a therapy that aims to treat atrial fibrillation. In particular, the efficacy of a therapy shall be assessed.

The therapy to be assessed can be any therapy that aims to treat atrial fibrillation. Preferably, said therapy is selected from the group consisting of administration of at least one anticoagulant, rhythm control, rate control, cardioversion and ablation. Said therapies are well known in the art and are e.g. reviewed in Fuster V et al. Circulation 2011; 123:e269-e367 which herewith is incorporated by reference in its entirety.

In an embodiment, the therapy is the administration of at least one anticoagulant, i.e. anticoagulation therapy, anticoagulation therapy is preferably a therapy which aims to reduce the risk of anticoagulation in said subject. Administration of at least one anticoagulant shall aim to reduce or prevent coagulation of blood and related stroke. In a preferred embodiment, at least one anticoagulant is selected from the group consisting of heparin, a coumarin derivative (i.e. a vitamin K antagonist), in particular warfarin or dicumarol, oral anticoagulants, in particular dabigatran, rivaroxaban or apixaban, tissue factor pathway inhibitor (TFPI), antithrombin III, factor IXa inhibitors, factor Xa inhibitors, inhibitors of factors Va and VIIIa and thrombin inhibitors (anti-IIa type). Accordingly, it is envisaged that the subject takes at least one of the aforementioned medicaments.

In preferred embodiment, the anticoagulant is a vitamin K antagonist such as warfarin or dicumarol. Vitamin K antagonists, such as warfarin or dicumarol are less expensive, but need better patient compliance, because of the inconvenient, cumbersome and often unreliable treatment with fluctuating time in therapeutic range. NOAC (new oral anticoagulants) comprise direct factor Xa inhibitors (apixaban, rivaroxaban, darexaban, edoxaban), direct thrombin inhibitors (dabigatran) and PAR-1 antagonists (vorapaxar, atopaxar).

In another preferred embodiment the anticoagulant and oral anticoagulant, in particular apixaban, rivaroxaban, darexaban, edoxaban, dabigatran, vorapaxar, or atopaxar.

Thus, the subject to be tested may be on therapy with an oral anticoagulant or a vitamin K antagonist at the time of the testing (i.e. at the time at which the sample is received.

In a preferred embodiment, the assessment of a therapy for atrial fibrillation is the monitoring of said therapy. In this embodiment, the reference amount is preferably the amount for BMP10 in an earlier obtained sample (i.e. in a sample that has been obtained prior to the test sample in step a).

Optionally, the amount of the at least one further biomarker as referred to herein is determined in addition to the amount of the BMP10-type peptide.

Accordingly, the present invention relates to a method for monitoring a therapy for atrial fibrillation in subject, said subject preferably suffering from atrial fibrillation, wherein said method comprises the steps of (a) determining, in at first sample from the subject, the amount of a BMP10-type peptide (Bone Morphogenic Protein 10-type peptide) and, optionally, the amount of at least one further biomarker selected from the group consisting of a natriuretic peptide, ESM-1 (Endocan), Ang2 (Angiopoietin 2) and FABP-3 (Fatty acid binding protein 3), (b) determining, in a second sample from the subject, the amount of the BMP10-type peptide and, optionally, the amount of at least one further biomarker selected from the group consisting of a natriuretic peptide, ESM-1 (Endocan), Ang2 (Angiopoietin 2) and FABP-3 (Fatty acid binding protein 3), wherein said second sample has been obtained after said first sample, (c) comparing the amount of the BMP10-type peptide in the first sample to the amount of the BMP10-type peptide in said second sample, and optionally comparing the amount of said at least one further biomarker in the first sample to the amount of said at least one further biomarker in said second sample, thereby monitoring anticoagulation therapy.

The term "monitoring" as used herein, preferably, relates to assessing the effects a therapy as referred to herein elsewhere. Thus, the efficacy of a therapy (such as anticoagulation therapy) is monitored.

The aforementioned method may comprise the further step of monitoring the therapy based on the results of the comparison step carried out in step c). As will be understood by those skilled in the art, the prediction of a risk is usually not intended to be correct for 100% of the subjects. The term, however, requires that prediction can be made for a statistically significant portion of subjects in a proper and correct manner. Thus, the actual monitoring may comprise further steps such as the confirmation.

Preferably, by carrying out the method of the present invention it can be assessed whether the subject responds to said therapy or not. A subject responds to a therapy if the condition the subject improves between obtaining the first and the second sample. Preferably, a subject does not respond to the therapy if the condition worsened between obtaining the first and the second sample.

Preferably, the first sample is obtained prior to the initiation of said therapy. More preferably, the sample is obtained within one week in particular within two weeks prior to the initiation of said therapy. However, it is also contemplated that the first sample may is obtained after initiation of said therapy (but before the second sample is obtained). In this case an ongoing therapy is monitored.

Thus, the second sample shall be obtained after the first sample. It is to be understood that the second sample shall be obtained after the initiation of said therapy.

Moreover, it is particularly contemplated that the second sample is obtained after a reasonable period of time after obtaining the first sample. It is to be understood, that the amounts of biomarkers referred herein, do not instantly change (e.g. within 1 minute or 1 hour) Therefore, "reasonable" in this context refers to intervals between obtaining the first and second sample which intervals allow the biomarker (s) to adjust. Therefore, the second sample, preferably, is obtained at least one month after said first sample, at least three months, or, in particular, at least six month after said first sample.

Preferably, a decrease and, more preferably, a significant decrease, and, most preferably, a statistically significant decrease of the amount(s) of the biomarker(s), i.e. of the BMP10-type peptide and optionally of the natriuretic peptide in the second sample as compared to the amount(s) of the biomarker(s) in the first sample is indicative for a subject who responds to the therapy. Thus, the therapy is efficient. Also preferably, no change of the concentration of the BMP10-type peptide or an increase, more preferably, a significant increase, most preferably, a statistically significant increase of the amount(s) of the biomarker(s) in the second sample as compared to the amount(s) of the biomarker(s) in the first sample is indicative for a subject who does not respond to the therapy. Thus, the therapy is not efficient.

The terms "significant" and "statistically significant" are known by the person skilled in the art. Thus, whether an increase or decrease is significant or statistically significant can be determined without further ado by the person skilled in the art using various well known statistic evaluation tools. For example, a significant increase or decrease is an increase or decrease of at least 10%, in particular of at least 20%.

A subject is considered to respond to the therapy, if the therapy reduces the risk of the subject of recurrence of atrial fibrillation. A subject is considered as not to respond to the therapy, if the therapy does not the risk of the subject of recurrence of atrial fibrillation.

In an embodiment, the intensity of the therapy is increased if the subject does not respond to the therapy. Moreover, it is envisaged that the intensity of the therapy is decreased, if a subject responds to the therapy. For example, the intensity of a therapy can be increased by increasing the dosage of the administered medicament. For example, the intensity of a therapy can be decreased by decreasing the dosage of the administered medicament. Thereby, it might be possible to avoid unwanted adverse side effects such as bleeding.

In another preferred embodiment, the assessment of a therapy for atrial fibrillation is the guidance of a therapy for atrial fibrillation. The term "guidance" as used herein, preferably, relates to adjusting the intensity of a therapy, such as increasing or decreasing the dose of oral anticoagulation, based on the determination of the biomarker, i.e. the BMP10-type peptide, during therapy.

In a further preferred embodiment, the assessment of a therapy for atrial fibrillation is the stratification of a therapy for atrial fibrillation. Thus, a subject shall be identified who is eligible to a certain therapy for atrial fibrillation. The term "stratification" as used herein, preferably, relates to selecting an adequate therapy based on the particular risk, molecular path identified and/or expected efficacy of the particular drug or procedure. Depending on the risk detected, particularly patients with minimal or no symptoms related to the arrhythmia will become eligible to control of the ventricular rate, cardioversion or ablation, who otherwise would receive only antithrombotic therapy.

The definitions and explanations given herein above apply mutatis mutandis to the following (except if stated otherwise), The present invention further concerns a method of aiding in the assessment of atrial fibrillation, said method comprising the steps of:

a) providing at least one sample from a subject, b) determining, in the at least one sample provided in step a), the amount of a BMP10-type peptide and, optionally, the amount of at least one further biomarker selected from the group consisting of a natriuretic peptide, ESM-1 (Endocan), Ang2 and FABP-3 (Fatty acid binding protein 3), and c) providing information on the determined amount of the BMP10-type peptide and optionally on the determined amount of the at least one further biomarker to a physician, thereby aiding in the assessment of atrial fibrillation.

The physician shall be the attending physician, i.e. the physician who requested the determination of the biomarker (s). The aforementioned method shall aid the attending physician in the assessment of atrial fibrillation. Thus, the method does not encompass the diagnosis, prediction, monitoring, differentiation, identification as referred to above in connection with the method of assessing atrial fibrillation.

Step a) of the aforementioned method of obtaining the sample does not encompass the drawing of the sample from the subject. Preferably, the sample is obtained by receiving a sample from said subject. Thus, the sample can have been delivered.

In an embodiment, the method above is a method of aiding in the prediction of stroke, said method comprising the steps of:

a) providing at least one sample from a subject as referred to herein in connection with the method of assessing atrial fibrillation, in particular in connection with the method of predicting atrial fibrillation, b) determining the amount of a BMP10-type peptide and the amount of at least one further biomarker selected from the group consisting of a natriuretic peptide, ESM-1 (Endocan), Ang2 and FABP-3 (Fatty acid binding protein 3), and c) providing information on the determined amount of the BMP10-type peptide and optionally on the determined amount of the at least one further biomarker to a physician, thereby aiding in the prediction of stroke.

The present invention further relates to a method, comprising:

a) providing an assay for a BMP10-type peptide and, optionally, at least one further assay for a further biomarker selected from the group consisting of a natriuretic peptide, ESM-1 (Endocan), Ang2 and FABP-3 (Fatty acid binding protein 3), and b) providing instructions for use of assay results obtained or obtainable by said assay(s) in the assessment of atrial fibrillation.

The purpose of the aforementioned method is, preferably, the aid in the assessment of atrial fibrillation.

The instructions shall contain a protocol for carrying out the method of assessing atrial fibrillation as described herein above. Further, the instructions shall contain at least one value for a reference amount for the BMP10-type peptide and optionally at least one value for a reference amount for a natriuretic peptide.

The "assay" is preferably a kit adapted for determining the amount of the biomarker. The term "kit" is explained herein below. E.g. said kit shall comprise at least one detection agent for a BMP10-type peptide and optionally and at least one further agent selected from the group consisting of an agent which specifically binds to a natriuretic peptide, an agent which specifically binds to ESM-1, an agent which specifically binds Ang2 and an agent which specifically binds to FABP-3. Thus, one to four detection agents may be present. The detection agents for the one to four biomarkers can be provided in a single kit or in separate kits.

The test result obtained or obtainable by said test, is the value for the amount of the biomarker(s).

In an embodiment, step b) comprises providing instructions for using of test results obtained or obtainable by said test(s) in prediction of stroke (as described herein elsewhere).

The present invention further pertains to computer-implemented method for assessing atrial fibrillation, comprising a) receiving, at a processing unit, a value for the amount of a BMP10-type peptide, and, optionally at least one further value for the amount of at least one further biomarker selected from the group consisting of a natriuretic peptide, ESM-1 (Endocan), Ang2 and FABP-3 (Fatty acid binding protein 3), wherein said amount of the BMP10-type peptide and, optionally, the amount of the at least one further biomarker have been determined in a sample from a subject, b) comparing, by said processing unit, the value or values received in step (a) to a reference or to references, and c) assessing atrial fibrillation based in the comparison step b).

The above-mentioned method is a computer-implemented method. Preferably, all steps of the computer-implemented method are performed by one or more processing units of a computer (or computer network). Thus, the assessment in step (c) is carried out by a processing unit. Preferably, said assessment is based on the results of step (b).

The value or values received in step (a) shall be derived from the determination of the amount of the biomarker from a subject as described elsewhere herein. Preferably, the value is a value for the concentration of the biomarker. The value will be typically received by the processing unit by uploading or sending the value to the processing unit. Alternatively, the value can be received by the processing unit by inputting the value via an user interface.

In an embodiment of the aforementioned method, the reference (or references) set forth in step (b) is (are) established from a memory. Preferably, a value for the reference is established from the memory.

In an embodiment of the aforementioned computer-implemented method of the present invention, the result of the assessment made in step c) is provided via a display, configured for presenting result.

In an embodiment of the aforementioned computer-implemented method of the present invention, the method may comprise the further step of transferring the information on the assessment made in step c) to the subject's electronic medical records.

Method of for the Diagnosis of Heart Failure

Further, is has been shown in the studies of the present invention that the determination of the amount of BMP10-type peptide in a sample from a subject allows for the diagnosis of heart failure. Accordingly, the present invention also contemplates a method for diagnosing heart failure based on the BMP10-type peptide (and optionally further based on a natriuretic peptide, ESM-1, Ang2 and/or FABP3.

The definitions given herein above in connection with the assessment of atrial fibrillation apply mutatis mutandis to the following (except if stated otherwise).

Accordingly, the present invention further relates to a method for diagnosing heart failure in a subject, said method comprising the steps of a) determining the amount of a BMP10-type peptide in a sample from the subject, and b) comparing the amount of the BMP10-type peptide to a reference amount, whereby heart failure is to be diagnosed.

The method for diagnosing heart failure may further comprise the determination the amount of at least one further biomarker selected from the group consisting of a natriuretic peptide, ESM-1 (Endocan), Ang2 (Angiopoietin 2) and FABP-3 (Fatty acid binding protein 3) and the comparison with a suitable reference amount.

Thus, the method for diagnosing heart failure may comprise the steps of:

a) determining, in at least one sample from the subject, the amount of a BMP10-type peptide (Bone Morphogenic Protein 10-type peptide) and, optionally, the amount of at least one further biomarker selected from the group consisting of a natriuretic peptide, ESM-1 (Endocan), Ang2 (Angiopoietin 2) and FABP-3 (Fatty acid binding protein 3), and b) comparing the amount of the BMP10-type peptide to a reference amount for the BMP10-type peptide and, optionally, comparing the amount of the at least one further biomarker to a reference amount for said at least one further biomarker, whereby heart failure is to be diagnosed.

The term "diagnosing" as used herein means assessing whether a subject as referred to in accordance with the method of the present invention suffers from heart failure, or not. The actual diagnosis whether a subject suffers from heart failure, or not, may comprise further steps such as the confirmation of a diagnosis. Thus, the diagnosis of heart failure is understood as an aid in the diagnosis of heart failure. Accordingly, the term "diagnosing" in the context of the present invention also encompasses aiding the physician to assess whether a subject suffers from heart failure, or not.

The term "heart failure" (abbreviated "HF") is well known by the skilled person. As used herein, the term preferably relates to an impaired systolic and/or diastolic function of the heart being accompanied by overt signs of heart failure as known to the person skilled in the art. Preferably, heart failure referred to herein is also chronic heart failure. Heart failure according to the present invention includes overt and/or advanced heart failure. In overt heart failure, the subject shows symptoms of heart failure as known to the person skilled in the art.

In an embodiment of present invention, the term "heart failure" refers to heart failure with reduced left ventricular ejection fraction (HFrEF). In another embodiment of present invention, the term "heart failure" refers to heart failure with preserved left ventricular ejection fraction (HFpEF).

HF can be classified into various degrees of severity. According to the NYHA (New York Heart Association) classification, heart failure patients are classified as belonging to NYHA classes I, II, III and IV. A patient having heart failure has already experienced structural and functional changes to his pericardium, myocardium, coronary circulation or cardiac valves. He will not be able to fully restore his health, and is in need of a treatment. Patients of NYHA Class I have no obvious symptoms of cardiovascular disease but already have objective evidence of functional impairment. Patients ofNYHA class II have slight limitation of physical activity. Patients ofNYHA class III show a marked limitation of physical activity. Patients of NYHA class IV are unable to carry out any physical activity without discomfort. They show symptoms of cardiac insufficiency at rest.

This functional classification is supplemented by the more recent classification by the American College of Cardiology and the American Heart Association (see J. Am. Coll. Cardiol. 2001; 38; 2101-2113, updated in 2005, see J. Am. Coll. Cardiol. 2005; 46; e1-e82). 4 stages A, B, C and D are defined. Stages A and B are not HF but are considered to help identify patients early before developing "truly" HF. Stages A and B patients are best defined as those with risk factors for the development of HF. For example, patients with coronary artery disease, hypertension, or diabetes mellitus who do not yet demonstrate impaired left ventricular (LV) function, hypertrophy, or geometric chamber distortion would be considered stage A, whereas patients who are asymptomatic but demonstrate LV hypertrophy and/or impaired LV function would be designated as stage B. Stage C then denotes patients with current or past symptoms of HF associated with underlying structural heart disease (the bulk of patients with HF), and stage D designates patients with truly refractory HF.

As used herein, the term "heart failure", preferably, includes stages A, B, C and D of the ACC/AHA classification referred to above. Also, the term includes NYHA class I, II, III and IV. Thus, the subject may or may not show typical symptoms of heart failure.

In a preferred embodiment, the term "heart failure" refers the heart failure stage A or, in particular, heart failure stage B according to the ACC/AHA classification referred to above. The identification of these early stages, in particular of stage A, is advantageous because treatment could be initiated before irreversible damage occurs.

The subject to be tested in accordance with the method of diagnosing heart failure preferably does not suffer from atrial fibrillation. However, it is also envisaged the subject suffers from atrial fibrillation. The term "atrial fibrillation" is defined in connection with the method of assessing heart failure.

Preferably, the subject to be tested in connection with the method of diagnosing heart failure is suspected to suffer heart failure.

The term "reference amount" has been defined in connection with the method of assessing atrial fibrillation. The reference amount that is applied in the method for diagnosing heart failure, in principle, can be determined as described above.

Preferably, an amount of the BMP10-type peptide (and optionally an amount of the at least one further biomarker such as ESM-1, Ang-2, FABP-3 and/or the natriuretic peptide) in the sample from a subject which is increased as compared to the reference amount is indicative for a subject suffering from heart failure and/or wherein an amount of the BMP10-type peptide (and optionally an amount of the at least one further biomarker such as ESM-1, Ang-2, FABP-3 and/or the natriuretic peptide) in the sample from a subject which is decreased as compared to the reference amount is indicative for a subject not suffering from heart failure.

In an embodiment of the method of diagnosing heart failure, said method further comprises a step of recommending and/or initiating a therapy for heart failure based on the results of the diagnosis. Preferably, a therapy is recommended or initiated if it is diagnosed that the subject suffers from heart failure. Preferably, the heart failure therapy comprises administration of at least one medicament selected from the group consisting of angiotensin converting enzyme (ACE) inhibitors, angiotensin II receptor blockers, beta blockers and aldosterone antagonists. Examples for angiotensin converting enzyme (ACE) inhibitors, angiotensin II receptor blockers, beta blockers and aldosterone antagonists are described in the next section.

Method for Predicting the Risk of a Subject of Hospitalization

It is known that some subjects progress more rapidly to heart failure, and thus are at elevated risk of hospitalization due to heart failure. It is important to identify these subjects as early as possible since this would allow for therapeutic measures that prevent or delay the progression to heart failure.

Advantageously, it has been found in the studies underlying the present invention that the amount of a BMP10-type in a sample of a subject allows for identifying subjects who are at risk of heart failure hospitalization. For example, subjects in the fourth quartile of BMP10 of the analyzed cohort (Example 4) had an about fourfold risk of heart failure hospitalization within a period of three years as compared to subjects in the first quartile.

Accordingly, the present invention further relates to a method for predicting the risk of a subject of hospitalization due to heart failure, said method comprising the steps of (a) determining, in at least one sample from the subject, the amount of a BMP10-type peptide (Bone Morphogenic Protein 10-type peptide), and, optionally, the amount of at least one further biomarker selected from the group consisting of a natriuretic peptide, ESM-1 (Endocan), Ang2 (Angiopoietin 2) and FABP-3 (Fatty acid binding protein 3), and (b) comparing the amount of the BMP10-type peptide to a reference amount for the BMP10-type peptide, and, optionally, comparing the amount of the at least one further biomarker to a reference amount for said at least one further biomarker The definitions and explanations made in connection the method of assessing atrial fibrillation and the method of diagnosing heart failure, preferably, apply to the method for predicting the risk of a subject of hospitalization due to heart failure The above method may further comprise step (c) of predicting the risk of a subject of hospitalization due to heart failure. Thus, steps (a), (b), (c) are preferably as follows:

(a) determining, in at least one sample from the subject, the amount of a BMP10-type peptide (Bone Morphogenic Protein 10-type peptide) and, optionally, the amount of at least one further biomarker selected from the group consisting of a natriuretic peptide, ESM-1 (Endocan), Ang2 (Angiopoietin 2) and FABP-3 (Fatty acid binding protein 3), and (b) comparing the amount of the BMP10-type peptide to a reference amount, and, optionally, comparing the amount of the at least one further biomarker to a reference amount for said at least one further biomarker, and (c) predicting the risk of a subject of hospitalization due to heart failure.

Preferably, the prediction is based on the results of the comparison in step (b).

The expression "hospitalization" is well understood by the skilled person and, preferably means that the subject is admitted to a hospital, in particular on an in-patient basis. The hospitalization should be due to heart failure. Thus, heart failure shall be the cause for the hospitalization. Preferably, the hospitalization is hospitalization due to acute or chronic heart failure. Thus, the heart failure includes both acute and chronic heart failure. More preferably, the hospitalization is hospitalization due to acute heart failure. Thus, the risk of a subject of hospitalization due to heart failure is predicted.

The term "heart failure" has been defined above. The definition applies accordingly. In some embodiments, the hospitalization is due heart failure classified as stage C or D according to according to the ACC/AHA classification. The ACC/AHA classification is well known in the art and described e.g. in Hunt et. al. (Journal of the American College of Cardiology, Volume 46, Issue 6, 20 Sep. 2005, Pages e1-e82, ACC/AHA Practice Guidelines) which is herewith incorporated by reference in its entirety.

In accordance with the aforementioned method, the risk of a subject of hospitalization due to heart failure shall be predicted. Thus, a subject can be identified who is at risk of hospitalization due to heart failure, or who is not at risk hospitalization due to heart failure. Accordingly, the term "predicting the risk" as used herein in accordance with the aforementioned method, preferably, refers to assessing the probability of hospitalization due to heart failure. In some embodiments, the above method of the present invention allows for differentiating between a subject at risk and a subject not at risk of hospitalization due to heart failure.

In accordance with the present invention, the term "predicting the risk" is understood as an aid in the prediction of the risk of hospitalization due to heart failure. The final prediction, in principle, will be carried out by physician and may include further diagnostic results.

As will be understood by those skilled in the art, the prediction of a risk is usually not intended to be correct for 100% of the subjects. The term, preferably, means that the prediction can be made for a statistically significant portion of subjects in a proper and correct manner. Whether a portion is statistically significant can be determined without further ado by the person skilled in the art using various well known statistic evaluation tools, e.g., determination of confidence intervals, p-value determination, Student's t-test, Mann-Whitney test etc. Details are found in Dowdy and Wearden, Statistics for Research, John Wiley & Sons, New York 1983. Preferred confidence intervals are at least 90%, at least 95%, at least 97%, at least 98%, or at least 99%. The p-values are, preferably, 0.1, 0.05, 0.01, 0.005, or 0.0001.

Preferably, the risk/probability within a certain time window is predicted. In some embodiments, said predictive window is calculated from the completion of the method of the present invention. In particular, said predictive window is calculated from the time point at which the sample to be tested has been obtained.

In a preferred embodiment of the present invention, the predictive window, preferably, is an interval of at least 1 year, at least 2 years, at least 3 years, at least 4 years, at least 5 years, or at least 10 years, or any intermitting time range. In another preferred embodiment of the present invention, the predictive window, preferably, is a period of up to 5 years, more preferably of up to 4 years, or most preferably, of up 3 years. Thus, the risk within a period of up to three, up to four or up to five years is predicted. Also, it is envisaged that the predictive window a period of 1 to 5 years. Alternatively, the predictive window may be a period of 1 to 3 years.

In a preferred embodiment, the risk of hospitalization due to heart failure within three years is predicted.

Preferably, the subject to be analyzed by the above method of the present invention is allocated either into the group of subjects being at risk of hospitalization due to heart failure, or into the group of subjects being not at risk of hospitalization due to heart failure. At subject who is at risk, preferably, is a subject who is at elevated risk of hospitalization due to heart failure (in particular within the predictive window). Preferably, said risk is elevated as compared to the risk in a cohort of subjects (i.e. a group of subjects). At subject who is not at risk, preferably, is a subject who is at reduced risk of hospitalization due to heart failure (in particular within the predictive window). Preferably, said risk is reduced as compared to the average risk in a cohort of subjects (i.e. a group of subjects). Accordingly, the method of the present invention allows for differentiating between an elevated risk and a reduced risk. A subject who is at risk of preferably has a risk of 12% or larger, or, more preferably of 15% or larger, or most preferably of 20% or larger of hospitalization due to heart failure, preferably, within a predictive window of 3 years. A subject who is not at risk preferably has a risk of lower than 10%, more preferably of lower than, 8%, or most preferably of lower than 7% of hospitalization due to heart failure, preferably, within a predictive window of 3 years.

The term “reference amount” has been defined elsewhere herein. The definition applies accordingly. The reference amount to be applied in the above method shall allow for predicting the risk of hospitalization due to heart failure. In some embodiments, the reference amount shall allow for differentiating between a subject who is at risk of hospitalization due to heart failure and a subject who is not at risk of hospitalization due to heart failure. In some embodiments, said reference amount is a predetermined value.

Preferably, an amount of the BMP10-type peptide in the sample from a subject which is increased as compared to the reference amount is indicative for a subject being at risk of hospitalization due to heart failure. Also preferably, an amount of the BMP10-type peptide in the sample from a subject which is decreased as compared to the reference amount is indicative for a subject who is not at risk of hospitalization due to heart failure.

If more than one biomarker is determined, the following applies:

Preferably, an amount of the BMP10-type peptide and an amount (or amounts) of the at least one further biomarker in the sample from a subject which is increased as compared to the respective reference amount is indicative for a subject being at risk of hospitalization due to heart failure. Also preferably, an amount of the BMP10-type peptide and an amount (or amounts) of the at least one further biomarker in the sample from a subject which is decreased as compared to the respective reference amount is indicative for a subject who is not at risk of hospitalization due to heart failure.

The term “sample” has been defined elsewhere herein. The definition applies accordingly. In some embodiments, the sample is a blood, serum or plasma sample.

The term “subject” has been defined elsewhere herein. The definition applies accordingly. In some embodiments, the subject is a human subject. Preferably, the subject to be tested is 50 years of age or older, more preferably 60 years of age or older, and most preferably 65 years of age or older. Further, it is envisaged that the subject to be tested is 70 years of age or older. Moreover, it is envisaged that the subject to be tested is 75 years of age or older. Also, the subject may be between 50 and 90 years.

In an embodiment, the subject to be tested a history of heart failure. In another embodiment, the subject to be tested has no history of heart failure.

The method of the present invention may aid personalized medicine. In a preferred embodiment, the above method for predicting the risk of a subject of hospitalization due to heart failure further comprises the step of recommending and/or initiating at least one suitable therapy, if it is predicted that the subject is at risk of hospitalization due to heart failure. Accordingly, the present invention also pertains to a method of treatment.

Preferably, term “therapy” as used in the context of the method for predicting the risk of a subject of hospitalization due to heart failure encompasses life style changes, diet regimen, interventions on the body as well as medicinal treatment, i.e. treatment with a medicament (or with medicaments). Preferably, the said therapy aims to reduce the risk of hospitalization due to heart failure. In an embodiment, the therapy is the administration ofa medicament (or medicaments). Preferably, the medicament is selected from the group consisting of an angiotensin-converting enzyme (ACE) inhibitor, an angiotensin receptor antagonist (ARB), an aldosterone antagonist and a beta blocker.

In some embodiments, the medicament is a beta blocker, such as are proprenolol, metoprolol, bisoprolol, carvedilol, bucindolol, and nebivolol. In some embodiments, the medicament is an ACE inhibitor, such as Enalapril, Captopril, Ramipril and Trandolapril. In some embodiments, the medicament is an angiotensin II receptor blocker, such as Losartan, Valsartan, Irbesartan, Candesartan, Telmisartan and Eprosartan. In some embodiments, the medicament is an aldosterone antagonist such as Eplerone, Spironolactone, Canrenone, Mexrenone and Prorenone.

Life style changes include smoking cessation, moderation of alcohol consumption, increased physical activity, weight loss, sodium (salt) restriction, weight management and healthy eating, daily fish oil, salt restriction.

Moreover, the present invention relates to the use (in particular, the in vitro use, e.g. in a sample from a subject) of i) a BMP10-type peptide and optionally of at least one further biomarker selected from the group consisting of a natriuretic peptide, ESM-1 (Endocan), Ang2 and FABP-3 (Fatty acid binding protein 3), and/or ii) at least one agent that specifically binds to a BMP10-type peptide, and, optionally, at least one further agent selected from the group consisting of an agent which specifically binds to a natriuretic peptide, an agent which specifically binds to ESM-1, an agent which specifically binds to Ang2 and an agent which specifically binds to FABP-3, for a) assessing atrial fibrillation b) predicting the risk of stroke in a subject, and/or c) diagnosing heart failure.

The terms mentioned in connection with the aforementioned use such as “sample”, “subject”, “detection agent”, “specifically binding”, “atrial fibrillation”, and “assessing atrial fibrillation” have been defined in connection with the method for assessing atrial fibrillation. The definitions and explanations apply accordingly.

The present invention further concerns the use (in particular, the in vitro use, e.g. in a sample from a subject) of a BMP10-type peptide, and/or of at least one agent that specifically binds to a BMP10-type peptide for predicting the risk of a subject of hospitalization due to heart failure.

Preferably, the aforementioned uses are an in vitro uses. Moreover, the detection agent is preferably and antibody such as a monoclonal antibody (or an antigen binding fragment thereof).

The present invention also relates to a kit. In an embodiment, the kit of the present invention comprises an agent which specifically binds to the a BMP10-type peptide and at least one further agent selected from the group consisting of an agent which specifically binds to a natriuretic peptide, an agent which specifically binds to ESM-1, an agent which specifically binds Ang2 and an agent which specifically binds to FABP-3.

Preferably, said kit is adapted for carrying out the method of the present invention, i.e. the method for assessing atrial fibrillation, or the method of diagnosing heart failure, or the method of predicting the risk of a subject of hospitalization due to heart failure. Optionally, said kit comprises instructions for carrying out the said method.

The term "kit" as used herein refers to a collection of the aforementioned components, preferably, provided separately or within a single container. The container also comprises instructions for carrying out the method of the present invention. These instructions may be in the form of a manual or may be provided by a computer program code which is capable of carrying out the calculations and comparisons referred to in the methods of the present invention and to establish the assessment or diagnosis accordingly when implemented on a computer or a data processing device. The computer program code may be provided on a data storage medium or device such as an optical storage medium (e.g., a Compact Disc) or directly on a computer or data processing device. Moreover, the kit may, preferably, comprise standard amounts for a BMP10-type peptide for calibration purposes. In a preferred embodiment, the kit further comprises standard amounts for the at least one further biomarker as referred to herein (such as the natriuretic peptide, or ESM-1) for calibration purposes In an embodiment, said kit is used for assessing atrial fibrillation in vitro. In an alternative embodiment, said kit is used for diagnosing heart failure in vitro. In an alternative embodiment, said kit is used for predicting the risk of hospitalization due to heart failure in vitro.

The figures show:

FIG. 1: Measurement of BMP10 ELISA in three patient groups (paroxysmal atrial fibrillation, persistent atrial fibrillation and patients in sinus rhythm)

Figure 2:
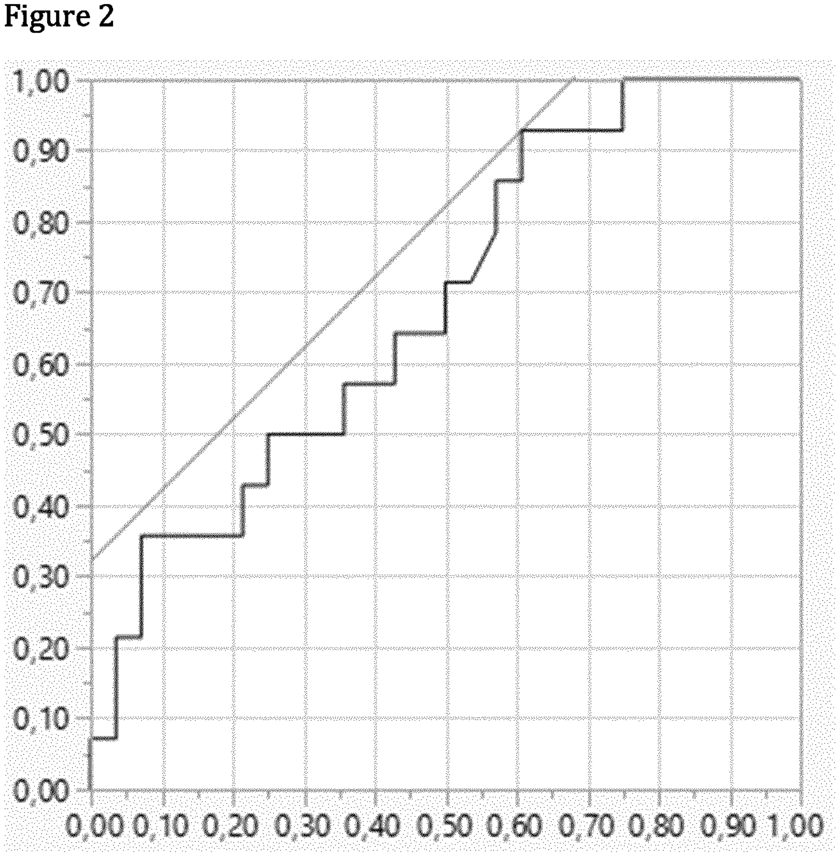

FIG. 2: ROC curve for BMP10 in paroxysmal Afib; AUC=0.68

FIG. 3: ROC curve for BMP10 in persistent Afib; AUC=0.90 (Exploratory AFib panel: Patients with a history of atrial fibrillation covering 14 cases of paroxysmal AFib, 16 cases of persistent Afib and 30 Controls)

FIG. 4: BMP10 in differentiation of patients with Heart Failure and patients without heart failure [unit: ng/ml]

Figure 5:
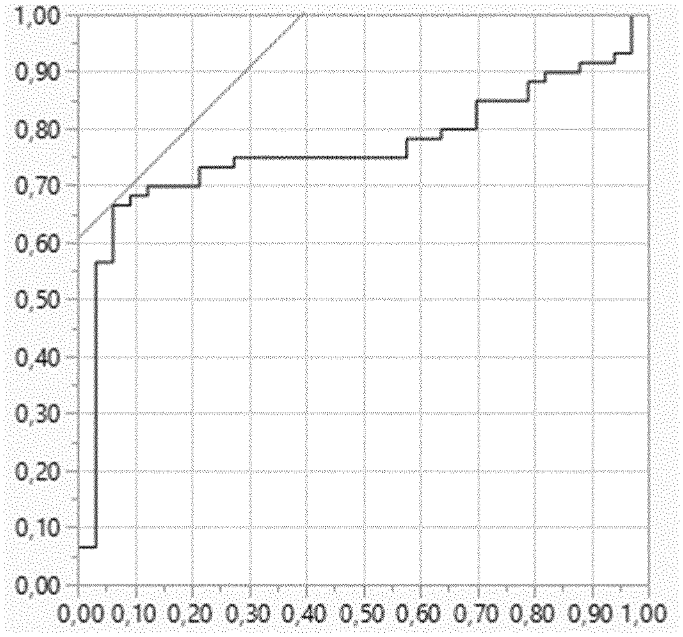

FIG. 5. BMP10 in differentiation of Heart Failure; ROC curve for BMP10; AUC=0.76

Figure 6:
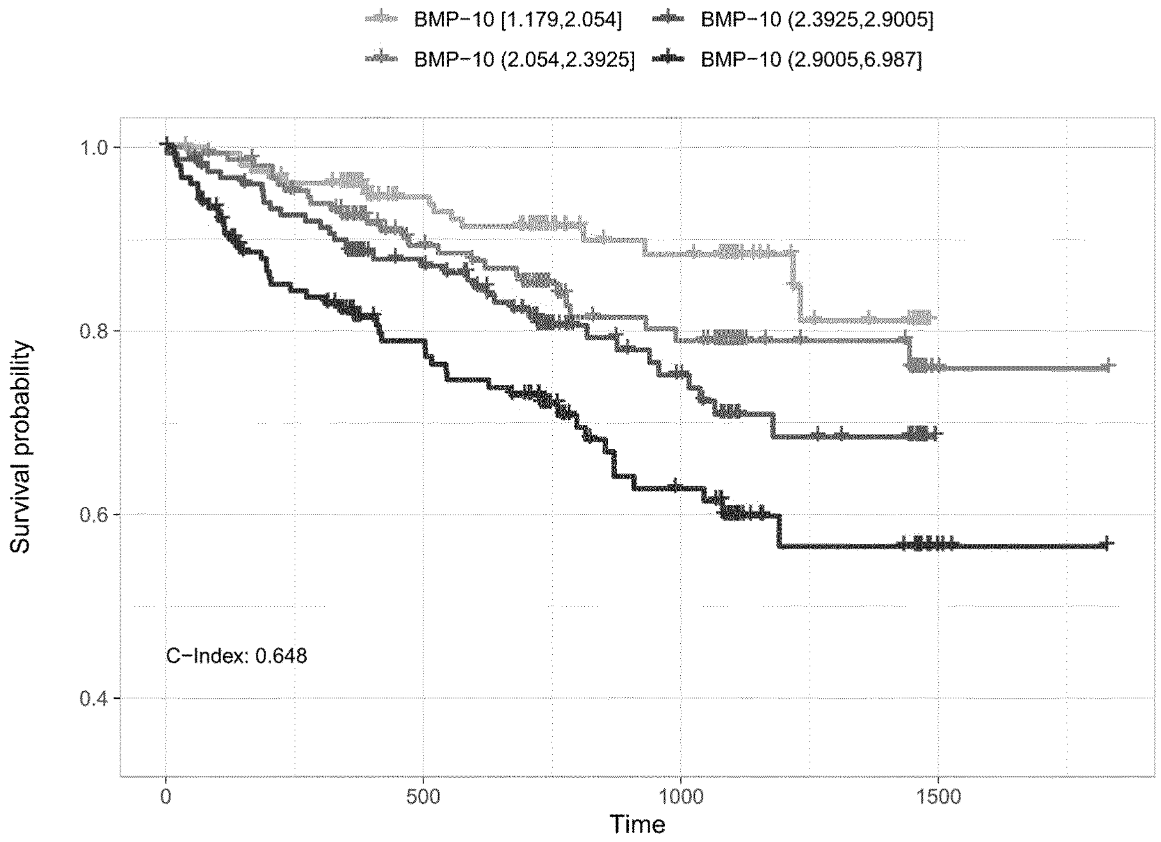

FIG. 6. Kaplan-Meier curve showing the risk for a HF hospitalization by quartiles of BMP-10 in patients with a prior history of heart failure.

Figure 7:
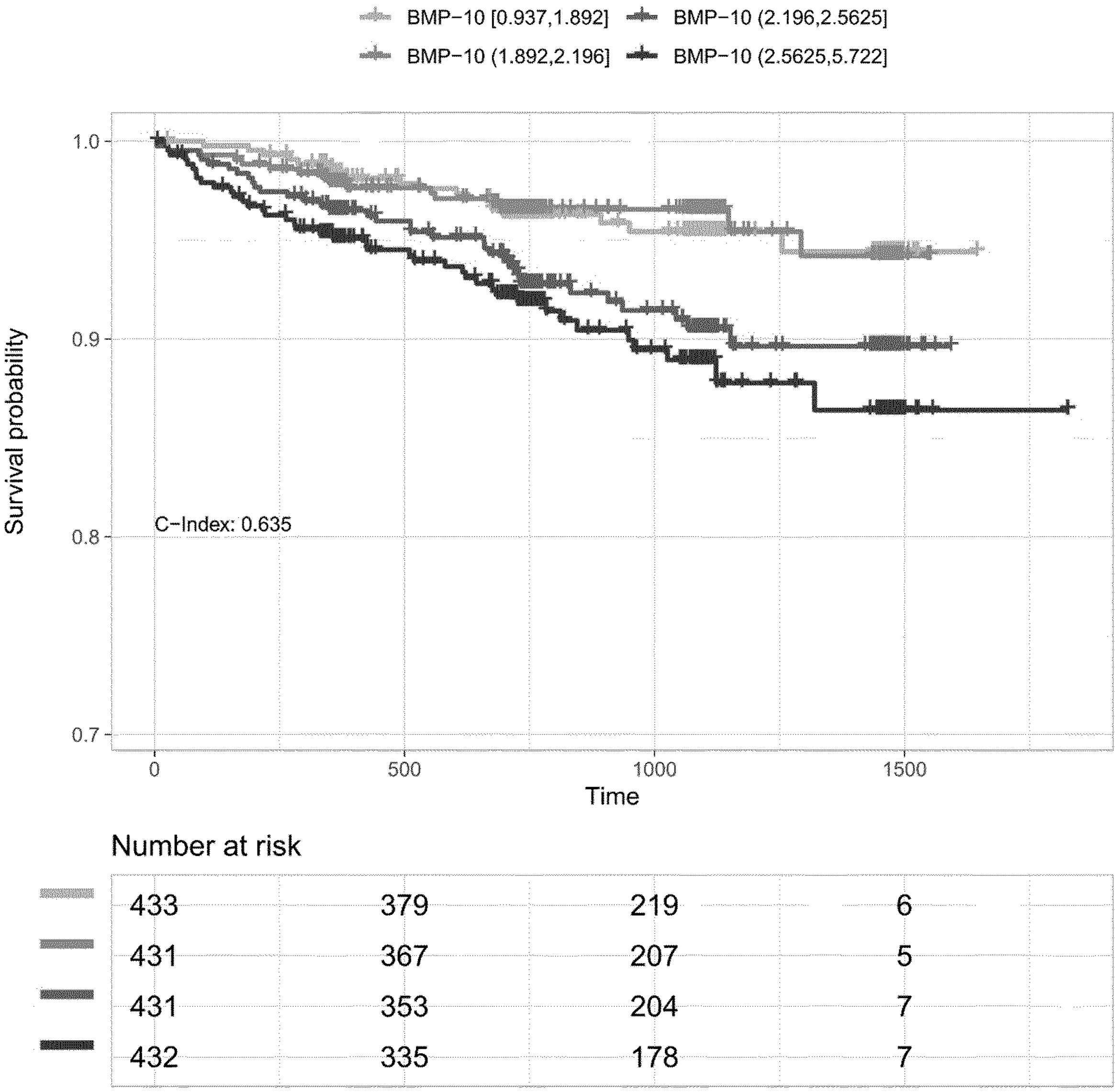

FIG. 7. Kaplan-Meier curve showing the risk for a HF hospitalization by quartiles of BMP-10 in patients without a prior history of heart failure.

Figure 8:
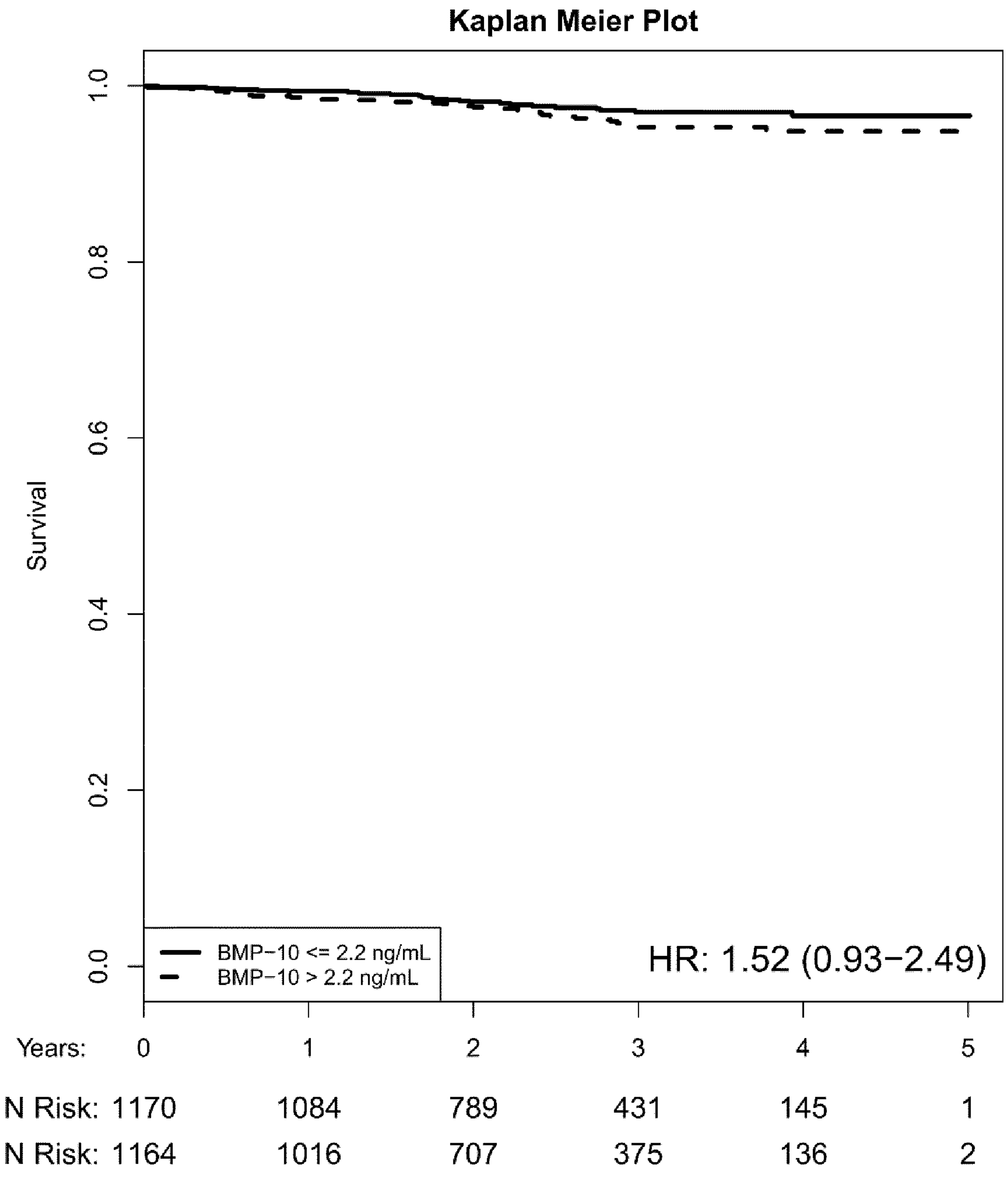

FIG. 8. Kaplan-Meier curve showing the risk for a stroke by dichotomized of BMP-10 (at median).

EXAMPLES

The invention will be merely illustrated by the following Examples. The said Examples shall, whatsoever, not be construed in a manner limiting the scope of the invention.

Example 1: Mapping Trial—Diagnose Patients with Atrial Fibrillation as Compared to Patients Based on their Different Circulating BMPO Levels The MAPPING study related to patients undergoing open chest surgery. Samples were obtained before anesthesia and surgery. Patients were electrophysiologically characterized using high-density epicardial mapping with multi-electrode arrays (high density mapping). The trial comprised 14 patients with paroxysmal atrial fibrillation, 10 patients with persistent atrial fibrillation and 28 controls, matched to best possible (on age, gender, comorbidities). BMP10 was determined in serum samples of the MAPPING study. Elevated BMP10 levels were observed in patients with atrial fibrillation versus controls. BMP10 levels were elevated in patients with paroxysmal atrial fibrillation versus matched controls, as well as in patients with persistent atrial fibrillation versus controls.

In addition, the biomarker ESM-1 was determined in samples from the MAPPING cohort. Interestingly, it was shown that the combined determination of BMP10 with ESM-1 allowed for an increase of the AUC to 0.92 for the differentiation between persistent AF vs. SR (sinus rhythm).

In addition, the biomarker FABP-3 was determined in samples from the MAPPING cohort. Interestingly, it was shown that the combined determination of BMP10 with FABP-3 allowed for an increase of the AUC to 0.73 for the differentiation between paroxysmal AF vs. SR (sinus rhythm).

Example 2: Heart Failure Panel

The heart failure panel included 60 patients with chronic heart failure. According to the ESC guidelines criteria, heart failure was diagnosed in patients with typical signs and symptoms and objective evidence of a structural or functional abnormality of the heart at rest. Patients between 18 and 80 years with ischemic or dilated cardiomyopathy or significant valvular disease and who were able to sign the consent form were included into the study. Patients with acute myocardial infarction, pulmonary embolism or stroke in the last 6 months, further with severe pulmonary hypertension and end stage renal disease were excluded. The patients suffered predominantly from heart failure stages NYHA II-IV.

The healthy control cohort included 33 subjects. The healthy status was verified by assessing status of ECG and echocardiography results. Participants with any abnormality were excluded.

Elevated BMP10 levels were observed in serum samples of patients with heart failure versus controls.

Example 3: Biomarker Measurements

BMP10 was measured in an research grade ECLIA assay for Bone Morphogenic Protein 10 (BMP10); ECLIA Assay from Roche Diagnostics, Germany.

For detection of BMP10 in human serum and plasma samples an antibody sandwich which specifically binds to the N-terminal prosegment of BMP10 was used. Such antibodies also bind to proBMP10 and preproBMP10. Thus, the sum of the amounts of the N-terminal prosegment of BMP10, proBMP10 and preproBMP10 was determined. Structural prediction based on findings from other BMP-type proteins as e.g. BMP9 show that BMP10 remains in a complex with proBMP10, thus detection of N-term prosegement also reflects the amount of BMP10. Moreover, the homodimeric form of BMP10 can be detected, as well as heterodimeric structures, as e.g. the combination with BMP9 or other BMP-type proteins.

Example 4: The SWISS AF Study—Risk Prediction of Heart Failure Hospitalization The data from the SWISS-AF study includes 2387 patients from which 617 have a history of heart failure (HF). BMP-10 was measured in these patients to assess its ability to predict the risk of a hospitalization due to heart failure.

As heart failure hospitalization can occur in patients with a history of heart failure and in patients without a known history heart failure the ability was assessed to predict future heart failure hospitalization was assessed in these groups independently. In total for 233 patients a hospitalization due to HF was recorded during follow-up. 125 of the 233 hospitalization occurred in patients with a prior known HF.

Prediction of HF Hospitalization in Patients with a Known History in HF

Table 1 shows the result of a cox proportional hazard model including in patients with a known history of HF. Dependent variable is the time until HF hospitalization and independent variable are log-2 the transformed BMP-10 values.

As visible by the hazard ratio and the low p-value BMP-10 is able to predict the risk for HF hospitalization significantly in patients with a known history of HF. As BMP-10 values were log-2 transformed before they were entered into the model the hazard ratio can interpreted that risk increase by 3.43 for a patient if the value of BMP-10 doubles

TABLE 1

Summary of cox proportional hazard model for BMP-10 (log-2 transformed) predicting the risk of HF hospitalization in patients with a known history of HF.

| Hazard Ratio | 95% Confidence Interval | P-Value |
|---|---|---|
| 3.43 | 2.23-05.27 | <0.001 |

FIG. 6 shows a Kaplan-Meier curve which displays the risk of HF hospitalization by quartiles of BMP-10. It is visible that the risk increases constantly with increasing BMP-10 values and the highest risk is observed for patients with BMP-10 levels within the highest quartile.

Prediction of HF Hospitalization in Patients without a Known History in HF

Table 2 shows the result of a cox proportional hazard model including in patients without a known history of HF. Dependent variable is the time until HF hospitalization and independent variable are the log-2 transformed BMP-10 values.

As visible by the hazard ratio and the low p-value BMP-10 is able to predict the risk for HF hospitalization significantly in patients without a known history of HF. As BMP-10 values were log-2 transformed before they were entered into the model the hazard ratio can interpreted that risk increase by 3.43 for a patient if the value of BMP-10 doubles

TABLE 2

Summary of cox proportional hazard model for BMP-10 (log-2 transformed) predicting the risk of HF hospitalization in patients without a known history of HF.

| Hazard Ratio | 95% Confidence Interval | P-Value |
|---|---|---|
| 4.24 | 2.52-7.15 | <0.001 |

FIG. 7 shows a Kaplan-Meier curve which displays the risk of HF hospitalization by quartiles of BMP-10. It is visible that the risk increases with increasing BMP-10 values and the risk is highest for patients with BMP-10 levels within the two highest quartiles.

Example 5: The SWISS AF Study—Risk Prediction of Stroke

The ability of circulating BMP10 to predict the risk for the occurrence of stroke was verified (in reference to example 3) in a prospective, multicentric registry of patients with documented atrial fibrillation (Conen D., Swiss Med Wkly. 2017 Jul. 10; 147:w14467). BMP10, results were available for 65 patients with an event and 2269 patients without an event.

In order to quantify the univariate prognostic value of BMP10 proportional hazard models were used with the outcome stroke.

The univariate prognostic performance of BMP10 was assessed by two different incorporations of the prognostic information given by BMP10.

The first proportional hazard model included BMP10 binarized at the median (2.2 ng/mL) and therefore comparing the risk of patients with BMP10 below or equal to the median versus patient with BMP10 above the median.

The second proportional hazard model included the original BMP10 levels but transformed to a log 2 scale. The log 2 transformation was performed in order to enable a better model calibration.

In order to get estimates for the absolute survival rates in the two groups based on the dichotomized baseline BMP10 measurement (<=2.2 ng/mL vs >2.2 ng/mL) a Kaplan-Meier plot was created.

In order to assess if the prognostic value of BMP10 is independent from known clinical and demographic risk factors a weighted proportional cox model including in addition the variables age, and history ofStroke/TIA/Thromboembolism was calculated. These were the only significant clinical risk predictors on the whole cohort (including all controls).

In order to assess the ability of BMP10 to improve existing risk scores for the prognosis of stroke the $CHADS_2$ the $CHA_2DS_2$-VASc and the ABC score were extended by BMP10 (log 2 transformed). Extension was done by creating a portioned hazard model including BMP10 and the respective risk score as independent variables.

The c-indices of the $CHADS_2$, the $CHA_2DS_2$-VASc and ABC score were compared to the c-indices of these extended models.

Results

Table 1 shows the results of the two univariate weighted proportional hazard models including the binarized or the log 2 transformed BMP10. The association between the risk for experiencing a stroke with the baseline value of BMP10 is not significant in the model using log 2-transformed BMP10 as a risk predictor but close to the significance level of 0.05.

For the model using the binarized BMP10 the p-value is slightly higher. It could be argued however with a higher number of events the effect could be statistically significant.

The hazard ration for the binarized BMP10 implies a 1.5-fold higher risk for a stroke in the patient group with baseline BMP10>2.2 ng/mL versus the patient group with baseline BMP10<=2.2 ng/mL. This can be seen also in FIG. 8 displaying the Kaplan Meier curves for the two groups.

The results of the proportional hazard model including BMP10 as log 2 transformed linear risk predictor suggest the log 2 transformed values BMP10 are proportional to the risk for experiencing a stroke. The hazard ratio of 2.038 can be interpreted in a way that a 2-fold decrease of BMP10 is associated with 2.038 increase of risk for a stroke.

TABLE 1

Results result of the univariate weighted proportional hazard model including the binarized and log2 transformed BMP10.

| | Hazard Ratio (HR) | 95%-CI HR | P-Value |
|---|---|---|---|
| BMP10 log2 | 1.523 | 0.930-2.495 | 0.095 |
| Baseline BMP10 <= 2.2 ng/mL vs BMP10 >2.2 ng/mL | 2.038 | 0.994-4.179 | 0.052 |

Table 2 shows the results of a proportional hazard model including BMP10 (log 2 transformed) in the combination with clinical and demographic variables. It is visible that the prognostic value of BMP10 diminishes to some extend but this could be partially also being explained by low statistical power of the model.

TABLE 2

Multivariate proportional hazard model including BMP10 and relevant clinical and demographic variables.

| | Hazard Ratio (HR) | 95%-C1 HR | P-Value |
|---|---|---|---|
| Age | 1.0615 | 1.0256-1.0987 | 0.0007 |
| History Stroke/TIA/embolism | 1.9186 | 1.1451-3.2145 | 0.0133 |
| BMP10 (log2 transformed) | 1.2253 | 0.5545-2.7076 | 0.6155 |

Table 3 shows the results of the weighted proportional hazard model combining the $CHADS_2$ score with BMP10 (log 2 transformed). In this model BMP10 can add prognostic information to the $CHADS_2$ score but with a p-value above 0.05 which can however be tolerated with respect to the low sample size.

TABLE 3

Weighted proportional hazard model combining the $CHADS_2$ score with BMP10 (log2 transformed)

| | Hazard Ratio (HR) | 95%-C1 HR | P-Value |
|---|---|---|---|
| $CHADS_2$ score | 1.3792 | 1.1590-1.6413 | 0.0003 |
| BMP10 (log2 transformed) | 1.5046 | 0.7094-3.1911 | 0.2869 |

Table 4 shows the results of the weighted proportional hazard model combining the $CHA_2DS_2$-VASc score with BMP10 (log 2 transformed). Also in this model BMP10 can add prognostic information to the $CHA_2DS_2$-VASc score but with a p-value above 0.05 which can however be tolerated with respect to the low sample size.

TABLE 4

Weighted proportional hazard model combining the $CHA_2DS_2$-VASc score with BMP10 (log2 transformed)

| | Hazard Ratio (HR) | 95%-C1 HR | P-Value |
|---|---|---|---|
| $CHA_2DS_2$-VASc score | 1.2756 | 1.0992-1.4803 | 0.1281 |
| BMP10 (log2 transformed) | 1.4308 | 0.6645-3.0806 | 0.3600 |

Table 5 shows the results of the weighted proportional hazard model combining the ABC score with BMP10 (log 2 transformed). In this model the estimated hazard ratio diminishes and BMP-10 likely can't add any prognostic performance

TABLE 5

Weighted proportional hazard model combining the ABC score with BMP10 (log2 transformed)

| | Hazard Ratio (HR) | 95%-C1 HR | P-Value |
|---|---|---|---|
| ABC score | 1.1839 | 1.1046-1.2688 | <0.0001 |
| BMP10 (log2 transformed) | 0.7321 | 0.3123-1.7161 | 0.4731 |

Table 6 shows the estimated c-indexes of BMP10 alone, of the $CHADS_2$, the $CHA_2DS_2$-VASc, the ABC score and of the weighted proportional hazard model combining the $CHADS_2$, the $CHA_2DS_2$-VASc, the ABC score with BMP10 (log 2) on the case cohort selection. It can be seen that the addition of BMP10 improves the c-index of the $CHADS_2$, the $CHA_2DS_2$-VASc score but not the ABC score.

The differences in c-index are 0.019, 0.015 and −0.002 for the $CHADS_2$, the $CHA_2DS_2$-VASc, the ABC score respectively.

TABLE 6

C-indexes of BMP10, the $CHA_2DS_2$-VASc score and the combination of the $CHA_2DS_2$-VASc score with BMP10 and C-indexes of the $CHADS_2$ and ABC score and their combination with BMP10.

| | C-Index |
|---|---|
| BMP10 univariate | 0.577 |
| $CHADS_2$ | 0.629 |
| $CHADS_2$ + BMP10 | 0.643 |
| $CHA_2DS_2$-VASc | 0.616 |
| $CHA_2DS_2$-VASc + BMP10 | 0.627 |
| ABC score | 0.692 |
| ABC score + BMP10 | 0.690 |

The invention claimed is:

1. A method for assessing atrial fibrillation in a subject, comprising the steps of a) measuring, in at least one sample from the subject, the amount of a BMP 10-type peptide (Bone Morphogenic Protein 10-type peptide) and, optionally, the amount of at least one further biomarker selected from the group consisting of a natriuretic peptide, ESM-1 (Endocan), Ang2 (Angiopoietin 2) and FABP3 (Fatty Acid Binding Protein 3), wherein the sample is selected from the group consisting of a blood, a serum, and a plasma sample, and b) comparing the amount of the BMP 10-type peptide to a reference amount for the BMP 10-type peptide from a control population that does not have atrial fibrillation and, optionally, comparing the amount of the at least one further biomarker to a reference amount for said at least one further biomarker, c) assessing that the subject has atrial fibrillation, wherein an elevated amount of the BMP 10-type peptide compared to the reference amount is indicative for a subject suffering from atrial fibrillation and/or wherein the amount of the BMP 10-type peptide below the reference amount is indicative for a subject not suffering from atrial fibrillation, and d) based on the assessment in step c), treating the subject by administering an anticoagulant to the subject.

2. The method of claim 1, wherein assessing that the subject has atrial fibrillation is the diagnosis of atrial fibrillation.

3. The method of claim 2, wherein the amount of the BMP 10-type peptide and an amount of the at least one further biomarker above the reference amount is indicative for a subject suffering from atrial fibrillation and/or wherein the amount of the BMP 10-type peptide and an amount of the at least one further biomarker below the reference amount is indicative for a subject not suffering from atrial fibrillation.

4. The method of claim 1, wherein the subject is suffering from atrial fibrillation, and wherein assessing that the subject has atrial fibrillation is the differentiation between paroxysmal and persistent atrial fibrillation.

5. The method of claim 4, wherein the amount of the BMP 10-type peptide and, optionally, the amount of the at least one further biomarker above the reference amount is indicative for a subject suffering from persistent atrial fibrillation and/or wherein the amount of the BMP 10-type peptide and, optionally, the amount of the at least one further biomarker below the reference amount is indicative for a subject suffering from paroxysmal atrial fibrillation.

6. The method of claim 1, wherein assessing that the subject has atrial fibrillation is the prediction of the risk of an adverse event associated with atrial fibrillation.

7. The method of claim 6, wherein the amount of the BMP 10-type peptide and, optionally, the amount of the at least one further biomarker above the reference amount is indicative for a subject who is at risk of suffering from an adverse event associated with atrial fibrillation and/or wherein the amount of the BMP 10-type peptide and, optionally, the amount of the at least one further biomarker below the reference amount is indicative for a subject who is not at risk of suffering from an adverse event associated with atrial fibrillation.

8. The method of claim 1, wherein assessing that the subject has atrial fibrillation is an assessment of a therapy for atrial fibrillation.

9. The method of claim 1, further comprising based on the assessment in claim 1 step c), recording the electrical activity of the heart of the subject by electrocardiogram and treating the subject based on the ECG results.

10. A method of aiding in the assessment of atrial fibrillation, said method comprising the steps of:

a) providing at least one sample from a subject, wherein the sample is selected from the group consisting of a blood, a serum, and a plasma sample, b) measuring in the at least one sample provided in step a), the amount of a BMP 10-type peptide (Bone Morphogenic Protein 10-type peptide) and, optionally, the amount of at least one further biomarker selected from the group consisting of a natriuretic peptide, ESM-1 (Endocan), Ang2 and FABP3 (Fatty Acid Binding Protein 3), c) comparing the amount of the BMP 10-type peptide to a reference amount for the BMP 10-type peptide from a control population that does not have atrial fibrillation and, optionally, comparing the amount of the at least one further biomarker to a reference amount for said at least one further biomarker, d) providing information on the measured amount of the BMP 10-type peptide and optionally on the measured amount of the at least one further biomarker to a physician, wherein an elevated amount of the BMP 10-type peptide compared to the reference amount is indicative for a subject suffering from atrial fibrillation, and e) based on the results of steps b), c) and d), treating the subject by administering an anticoagulant to the subject.

11. A method for diagnosing heart failure in a subject, said method comprising the steps of (a) measuring in at least one sample from the subject, the amount of a BMP 10-type peptide (Bone Morphogenic Protein 10-type peptide) and, optionally, the amount of at least one further biomarker selected from the group consisting of a natriuretic peptide, ESM-1 (Endocan), Ang2, and FABP3 (Fatty Acid Binding Protein 3), (b) comparing the amount of the BMP 10-type peptide to a reference amount for the BMP 10-type peptide from a control population that does not have heart failure and, optionally, comparing the amount of the at least one further biomarker to a reference amount for said at least one further biomarker, (c) diagnosing heart failure in the subject, wherein an elevated amount of the BMP 10-type peptide compared to the reference amount is indicative for a subject suffering from heart failure and/or wherein the amount of the BMP 10-type peptide below the reference amount is indicative for a subject not suffering from heart failure, and (d) based on the diagnosis in step (c), treating the subject with a therapy selected from the group consisting of an angiotensin-converting enzyme (ACE) inhibitor, an angiotensin receptor antagonist (ARB), an aldosterone antagonist, and a beta blocker.

12. A method of assessing atrial fibrillation or diagnosing heart failure in a subject, said method comprising the steps of:

(a) measuring in vitro, in at least one sample from the subject, the amount of a BMP 10-type peptide and optionally of at least one further biomarker selected from the group consisting of a natriuretic peptide, ESM-1 (Endocan), Ang2 and FABP3 (Fatty Acid Binding Protein 3), wherein the sample is selected from the group consisting of a blood, a serum, and a plasma sample, (b) comparing to a reference amount from a control population that does not have atrial fibrillation or heart failure the amount of BMP 10-type peptide and optionally at least one further biomarker selected from the group consisting of a natriuretic peptide, ESM-1 (Endocan), Ang2 and FABP3 (Fatty Acid Binding Protein 3), (c) assessing atrial fibrillation or diagnosing heart failure in the subject, wherein an elevated amount of the BMP 10-type peptide compared to the reference amount is indicative for a subject suffering from atrial fibrillation or heart failure and/or wherein the amount of the BMP 10-type peptide below the reference amount is indicative for a subject not suffering from atrial fibrillation or heart failure, and (d) based on the assessment or diagnosis in step (c), treating the subject with a treatment comprising:

(i) when atrial fibrillation is assessed, administering an anticoagulant to the subject, or (ii) when heart failure is diagnosed, a therapy selected from the group consisting of an angiotensin-converting enzyme (ACE) inhibitor, an angiotensin receptor antagonist (ARB), an aldosterone antagonist, and a beta blocker.

13. A method of detecting a BMP 10-type peptide in a subject, the method comprising:

providing a sample from the subject, wherein the sample is selected from the group consisting of a blood, a serum, and a plasma sample, wherein the subject has atrial fibrillation or heart failure, and detecting whether a BMP 10-type peptide is present in the sample.

14. The method of claim 13, further comprising detecting the presence of at least one further biomarker selected from the group consisting of a natriuretic peptide, ESM-1 (Endocan), Ang2 (Angiopoietin 2), and FABP3 (Fatty Acid Binding Protein 3).

15. A method of detecting an elevated amount or concentration of a BMP 10-type peptide in a subject, the method comprising:

providing a sample from the subject, wherein the sample is selected from the group consisting of a blood, a serum, and a plasma sample, wherein the subject has atrial fibrillation or heart failure, and detecting the elevated amount or concentration of a BMP 10-type peptide in the sample of the subject.

16. A method for measuring the amount of a BMP 10-type peptide in a sample from a subject, the method comprising:

providing the sample from the subject, wherein the sample is selected from the group consisting of a blood, a serum, and a plasma sample, wherein the subject has atrial fibrillation or heart failure, measuring the amount of a BMP 10-type peptide in the sample of the subject.

* * * * *

SEQUENCE LISTING

<160> NUMBER OF SEQ ID NOS: 1

<210> SEQ ID NO 1
<211> LENGTH: 424
<212> TYPE: PRT
<213> ORGANISM: Homo sapiens
<220> FEATURE:
<223> OTHER INFORMATION: unprocessed preproBMP10

<400> SEQUENCE: 1

Met Gly Ser Leu Val Leu Thr Leu Cys Ala Leu Phe Cys Leu Ala Ala
1 5 10 15

Tyr Leu Val Ser Gly Ser Pro Ile Met Asn Leu Glu Gln Ser Pro Leu
20 25 30

Glu Glu Asp Met Ser Leu Phe Gly Asp Val Phe Ser Glu Gln Asp Gly
35 40 45

Val Asp Phe Asn Thr Leu Leu Gln Ser Met Lys Asp Glu Phe Leu Lys
50 55 60

Thr Leu Asn Leu Ser Asp Ile Pro Thr Gln Asp Ser Ala Lys Val Asp
65 70 75 80

Pro Pro Glu Tyr Met Leu Glu Leu Tyr Asn Lys Phe Ala Thr Asp Arg
85 90 95

Thr Ser Met Pro Ser Ala Asn Ile Ile Arg Ser Phe Lys Asn Glu Asp
100 105 110

Leu Phe Ser Gln Pro Val Ser Phe Asn Gly Leu Arg Lys Tyr Pro Leu
115 120 125

Leu Phe Asn Val Ser Ile Pro His His Glu Glu Val Ile Met Ala Glu
130 135 140

Leu Arg Leu Tyr Thr Leu Val Gln Arg Asp Arg Met Ile Tyr Asp Gly
145 150 155 160

Val Asp Arg Lys Ile Thr Ile Phe Glu Val Leu Glu Ser Lys Gly Asp
165 170 175

Asn Glu Gly Glu Arg Asn Met Leu Val Leu Val Ser Gly Glu Ile Tyr
180 185 190

Gly Thr Asn Ser Glu Trp Glu Thr Phe Asp Val Thr Asp Ala Ile Arg
195 200 205

Arg Trp Gln Lys Ser Gly Ser Ser Thr His Gln Leu Glu Val His Ile
210 215 220

Glu Ser Lys His Asp Glu Ala Glu Asp Ala Ser Ser Gly Arg Leu Glu
225 230 235 240

Ile Asp Thr Ser Ala Gln Asn Lys His Asn Pro Leu Leu Ile Val Phe
245 250 255

Ser Asp Asp Gln Ser Ser Asp Lys Glu Arg Lys Glu Glu Leu Asn Glu
260 265 270

Met Ile Ser His Glu Gln Leu Pro Glu Leu Asp Asn Leu Gly Leu Asp
275 280 285

Ser Phe Ser Ser Gly Pro Gly Glu Glu Ala Leu Leu Gln Met Arg Ser
290 295 300

Asn Ile Ile Tyr Asp Ser Thr Ala Arg Ile Arg Arg Asn Ala Lys Gly
305 310 315 320

Asn Tyr Cys Lys Arg Thr Pro Leu Tyr Ile Asp Phe Lys Glu Ile Gly
325 330 335

Trp Asp Ser Trp Ile Ile Ala Pro Pro Gly Tyr Glu Ala Tyr Glu Cys
340 345 350

Arg Gly Val Cys Asn Tyr Pro Leu Ala Glu His Leu Thr Pro Thr Lys
355 360 365

His Ala Ile Ile Gln Ala Leu Val His Leu Lys Asn Ser Gln Lys Ala
370 375 380

Ser Lys Ala Cys Cys Val Pro Thr Lys Leu Glu Pro Ile Ser Ile Leu
385 390 395 400

Tyr Leu Asp Lys Gly Val Val Thr Tyr Lys Phe Lys Tyr Glu Gly Met

-continued

```
                    405                      410                      415

Ala Val Ser Glu Cys Gly Cys Arg
              420
```